(12) United States Patent
Meglan

(10) Patent No.: US 11,723,718 B2
(45) Date of Patent: Aug. 15, 2023

(54) THERAPY DELIVERY SYSTEM THAT OPERATES ON THE SURFACE OF AN ANATOMICAL ENTITY

(71) Applicant: Dwight Alan Meglan, Westwood, MA (US)

(72) Inventor: Dwight Alan Meglan, Westwood, MA (US)

(73) Assignee: HEARTLANDER SURGICAL, INC., Westwood, MA (US)

( * ) Notice: Subject to any disclaimer, the term of this patent is extended or adjusted under 35 U.S.C. 154(b) by 804 days.

(21) Appl. No.: 15/172,124

(22) Filed: Jun. 2, 2016

(65) Prior Publication Data

US 2016/0367312 A1 Dec. 22, 2016

Related U.S. Application Data

(60) Provisional application No. 62/170,097, filed on Jun. 2, 2015.

(51) Int. Cl.
*A61B 18/14* (2006.01)
*A61B 34/10* (2016.01)
(Continued)

(52) U.S. Cl.
CPC ...... *A61B 18/1477* (2013.01); *A61B 18/1492* (2013.01); *A61B 34/10* (2016.02);
(Continued)

(58) Field of Classification Search
CPC . A61B 18/1477; A61B 34/10; A61B 18/1492; A61B 2034/107; A61B 34/72;
(Continued)

(56) References Cited

U.S. PATENT DOCUMENTS 5,022,399 A * 6/1991 Biegeleisen ........... A61B 1/042
600/439
5,662,587 A 9/1997 Gru et al.
(Continued)

FOREIGN PATENT DOCUMENTS

JP 1487050 6/2010

OTHER PUBLICATIONS

Rosen, Jacob, editor. Surgical Robotics—2011. Springer New York, 2011. pp. 573-575.*
(Continued)

*Primary Examiner* — Jaymi E Della
(74) *Attorney, Agent, or Firm* — Onello & Mello, LLP

(57) ABSTRACT

Techniques for performing therapy using an internal anatomy therapy delivery system are described herein. The internal anatomy therapy delivery system calculates a treatment location from sensor data received from an internal anatomy therapy delivery device, determines an appropriate therapy, and moves the internal anatomy therapy delivery device to a location on the anatomical surface corresponding to the therapy. Once at the location, the internal anatomy therapy delivery device determines treatment parameters based on local measurements, delivers the treatment, and makes additional measurements to determine whether the treatment was successful.

28 Claims, 20 Drawing Sheets

(51) Int. Cl.
*A61B 18/00* (2006.01)
*A61B 34/00* (2016.01)

(52) U.S. Cl.
CPC ..... *A61B 34/72* (2016.02); *A61B 2018/00363* (2013.01); *A61B 2018/00577* (2013.01); *A61B 2018/00839* (2013.01); *A61B 2018/00982* (2013.01); *A61B 2034/107* (2016.02)

(58) Field of Classification Search
CPC ........... A61B 2018/00363; A61B 2018/00577; A61B 2018/00839; A61B 2018/00982
See application file for complete search history.

(56) References Cited

U.S. PATENT DOCUMENTS

| | | | |
|---|---|---|---|
| 5,733,280 A * | 3/1998 | Avitall | A61B 18/02 606/20 |
| 5,906,591 A | 5/1999 | Dario et al. | |
| 5,906,607 A | 5/1999 | Taylor et al. | |
| 5,979,453 A * | 11/1999 | Savage | A61B 18/1477 128/898 |
| 6,231,585 B1 | 5/2001 | Takahashi et al. | |
| 6,589,166 B2 | 7/2003 | Knight et al. | |
| 6,719,684 B2 | 4/2004 | Kim et al. | |
| 6,786,898 B2 | 9/2004 | Guenst | |
| 6,824,508 B2 | 11/2004 | Kim et al. | |
| 6,887,238 B2 | 5/2005 | Jahns et al. | |
| 6,890,292 B2 | 5/2005 | Kochamba et al. | |
| 7,018,328 B2 | 3/2006 | Mager et al. | |
| 7,052,493 B2 | 5/2006 | Yaska et al. | |
| 7,146,225 B2 | 12/2006 | Guenst et al. | |
| 7,186,262 B2 | 3/2007 | Saadat | |
| 7,237,555 B2 | 7/2007 | Kochamba et al. | |
| 7,250,028 B2 | 7/2007 | Julian et al. | |
| 7,326,177 B2 | 2/2008 | Williamson, IV et al. | |
| 7,338,441 B2 | 3/2008 | Houser et al. | |
| 7,373,197 B2 | 5/2008 | Daighighian et al. | |
| 7,377,895 B2 | 5/2008 | Spence et al. | |
| 7,485,090 B2 | 2/2009 | Taylor | |
| 7,503,891 B2 | 3/2009 | Green, II et al. | |
| 7,507,235 B2 | 3/2009 | Keogh et al. | |
| 8,105,235 B2 | 1/2012 | Ramans et al. | |
| 8,162,925 B2 | 4/2012 | Riviere et al. | |
| 8,277,476 B2 | 10/2012 | Taylor et al. | |
| 8,535,304 B2 | 9/2013 | Sklar et al. | |
| 9,265,582 B2 | 2/2016 | Riviere et al. | |
| 2002/0042594 A1* | 4/2002 | Lum | A61B 18/14 604/117 |
| 2002/0115911 A1 | 8/2002 | Knight et al. | |
| 2002/0138109 A1 | 9/2002 | Keogh et al. | |
| 2002/0165434 A1 | 11/2002 | Williamson, IV et al. | |
| 2002/0168317 A1 | 11/2002 | Daighighian et al. | |
| 2002/0171385 A1 | 11/2002 | Kim et al. | |
| 2003/0018358 A1 | 1/2003 | Saadat | |
| 2003/0060685 A1 | 3/2003 | Houser et al. | |
| 2003/0088150 A1 | 5/2003 | Green, II et al. | |
| 2003/0092964 A1 | 5/2003 | Kim et al. | |
| 2003/0125604 A1 | 7/2003 | Kochamba et al. | |
| 2003/0158463 A1 | 8/2003 | Julian et al. | |
| 2003/0167056 A1* | 9/2003 | Jahns | A61B 18/1492 606/41 |
| 2004/0015047 A1 | 1/2004 | Mager et al. | |
| 2004/0054363 A1 | 3/2004 | Vaska et al. | |
| 2004/0088035 A1 | 5/2004 | Guenst et al. | |
| 2004/0092798 A1 | 5/2004 | Spence et al. | |
| 2004/0138526 A1 | 7/2004 | Guenst | |
| 2004/0171917 A1 | 9/2004 | Paul et al. | |
| 2004/0230099 A1 | 11/2004 | Taylor et al. | |
| 2005/0033270 A1 | 2/2005 | Ramans et al. | |
| 2005/0181119 A1 | 3/2005 | Kochamba et al. | |
| 2005/0119640 A1 | 6/2005 | Sverduk et al. | |
| 2005/0154376 A1* | 7/2005 | Riviere | A61B 1/00156 606/1 |
| 2005/0261673 A1 | 11/2005 | Bonner et al. | |
| 2005/0288566 A1* | 12/2005 | Levendusky | A61B 1/2736 600/372 |
| 2007/0123748 A1 | 5/2007 | Meglan | |
| 2007/0185485 A1* | 8/2007 | Hauck | A61B 5/6885 606/41 |
| 2007/0249999 A1* | 10/2007 | Sklar | A61M 25/0113 604/101.05 |
| 2008/0009747 A1* | 1/2008 | Saadat | A61B 1/04 600/471 |
| 2008/0082109 A1* | 4/2008 | Moll | A61B 34/30 606/130 |
| 2010/0114093 A1* | 5/2010 | Mahapatra | A61B 18/1492 606/41 |
| 2010/0137704 A1* | 6/2010 | Vij | A61B 5/0555 600/422 |
| 2010/0217117 A1* | 8/2010 | Glossop | A61B 8/4245 600/424 |
| 2010/0240955 A1* | 9/2010 | Sinai | A61B 1/00156 600/116 |
| 2011/0087175 A1* | 4/2011 | Krishnan | A61B 5/06 604/272 |
| 2011/0288540 A1* | 11/2011 | Wright | A61B 18/1477 606/33 |
| 2011/0295268 A1* | 12/2011 | Roel | A61B 34/30 606/130 |
| 2012/0016291 A1* | 1/2012 | Hlavka | A61B 34/71 604/21 |
| 2012/0120091 A1* | 5/2012 | Koudijs | A61B 90/10 345/589 |
| 2012/0271318 A1* | 10/2012 | Riviere | A61B 34/30 606/130 |
| 2014/0052117 A1* | 2/2014 | Curley | A61B 18/04 606/29 |

OTHER PUBLICATIONS

Ota T, Patronik NA, Schwartzman D, Riviere ON, Zenati MA. Minimally invasive epicardial injections using a novel semiautonomous robotic device. Circulation. Sep. 30, 2008;118(14 Suppl):S115-20. doi: 10.1161/CIRCULATIONAHA.107.756049. PMID: 18824742; PMCID: PMC2832072. (Year: 2010).*

O'Connell, F. "Robots With Moves More Delicate Than a Surgeon's", The New York Times (Jun. 5, 2007). Accessed on the internet on Jul. 11, 2022: https://archive.nytimes.com/www.nytimes.com/imagepages/2007/06/05/science/05science_graphic.html.

International Search Report and Written Opinion dated Feb. 16, 2022 issued in corresponding International Application No. PCT/US2021/061733.

* cited by examiner

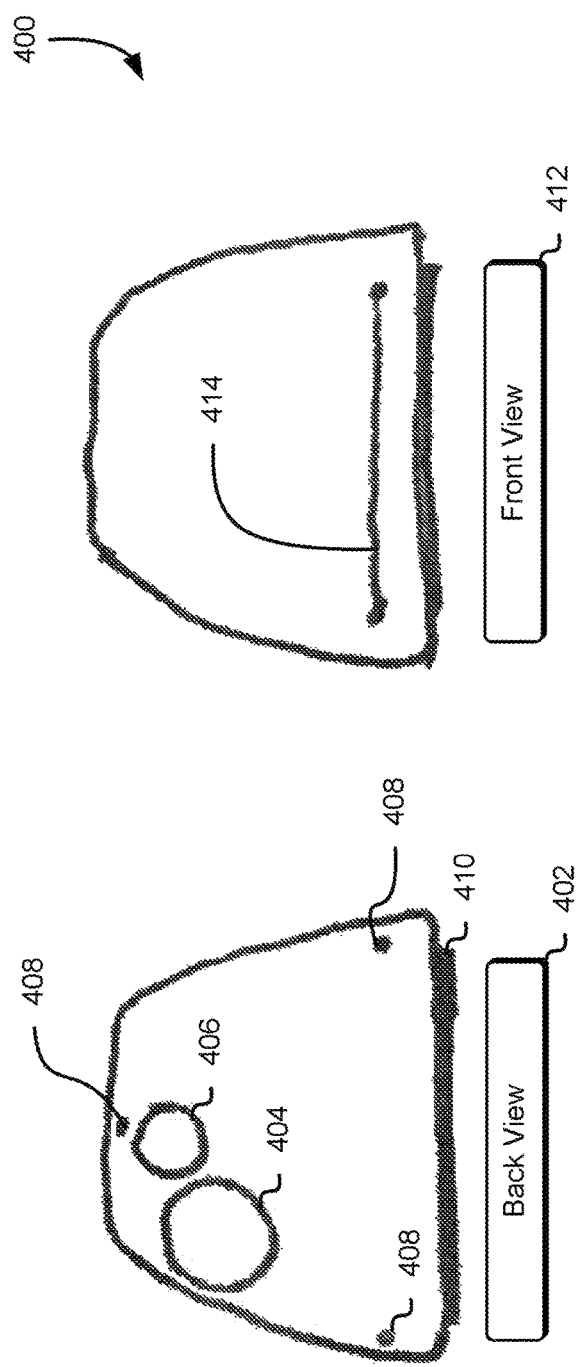
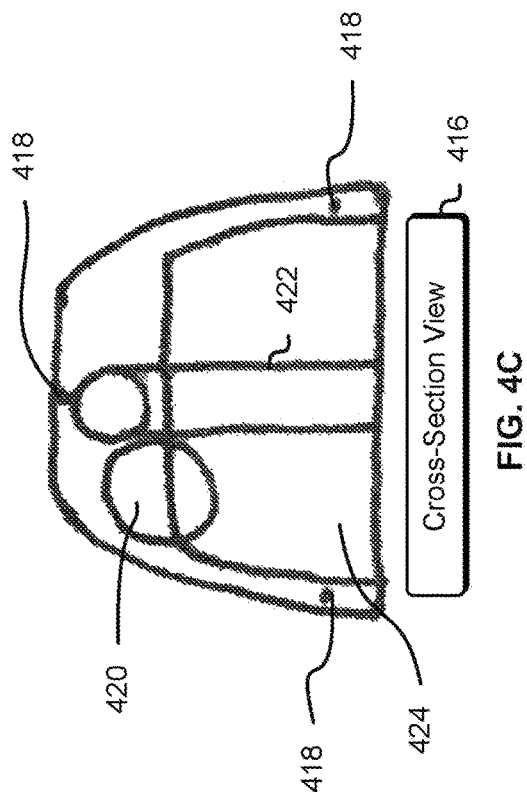

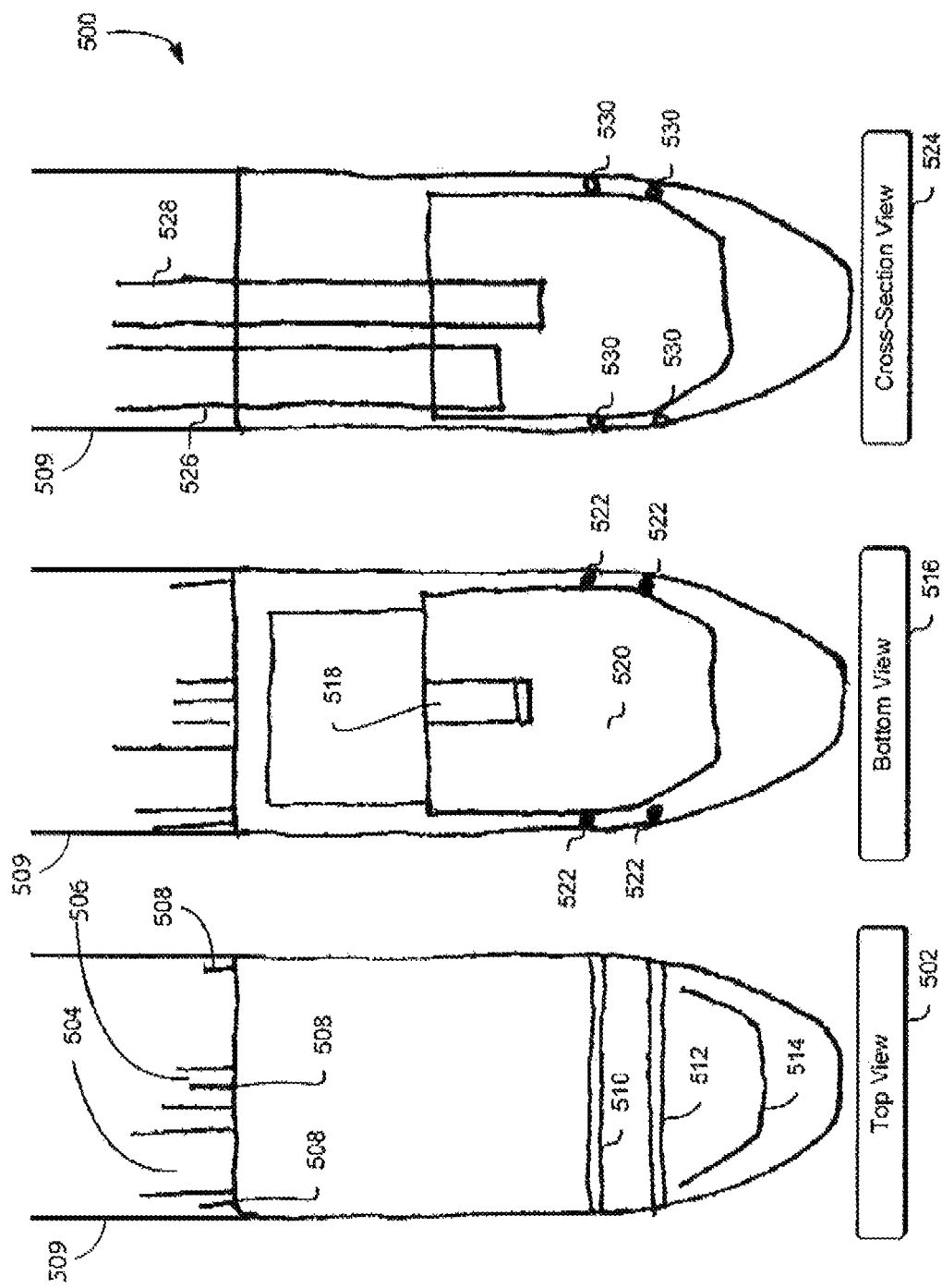

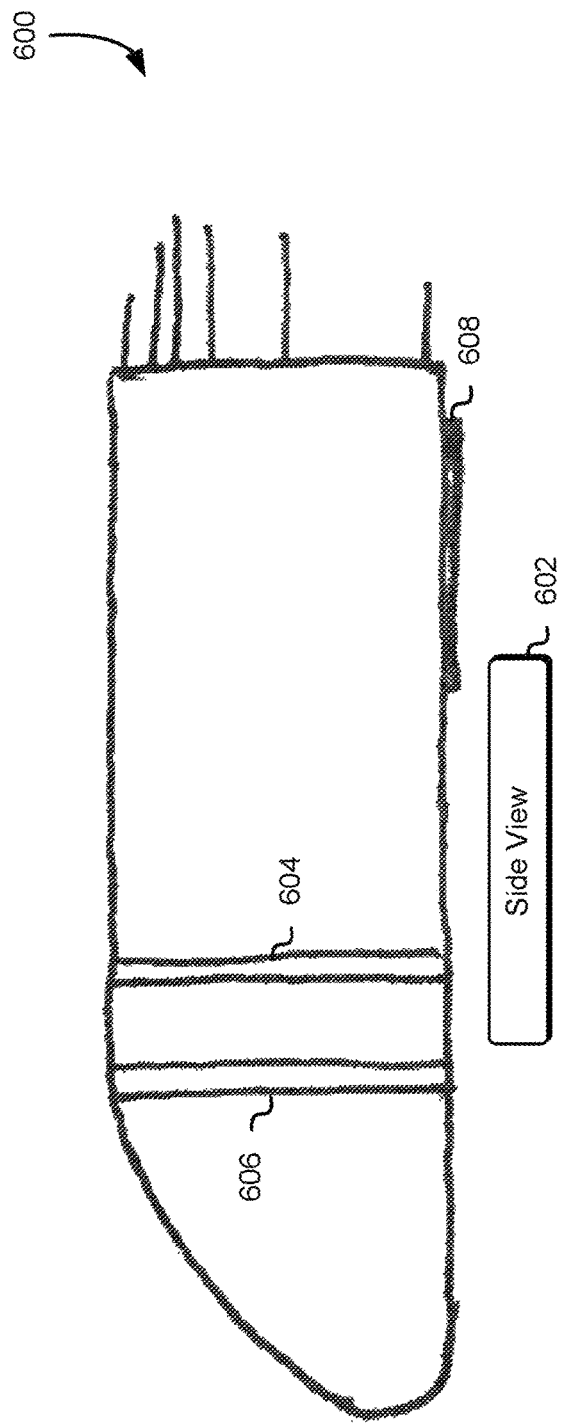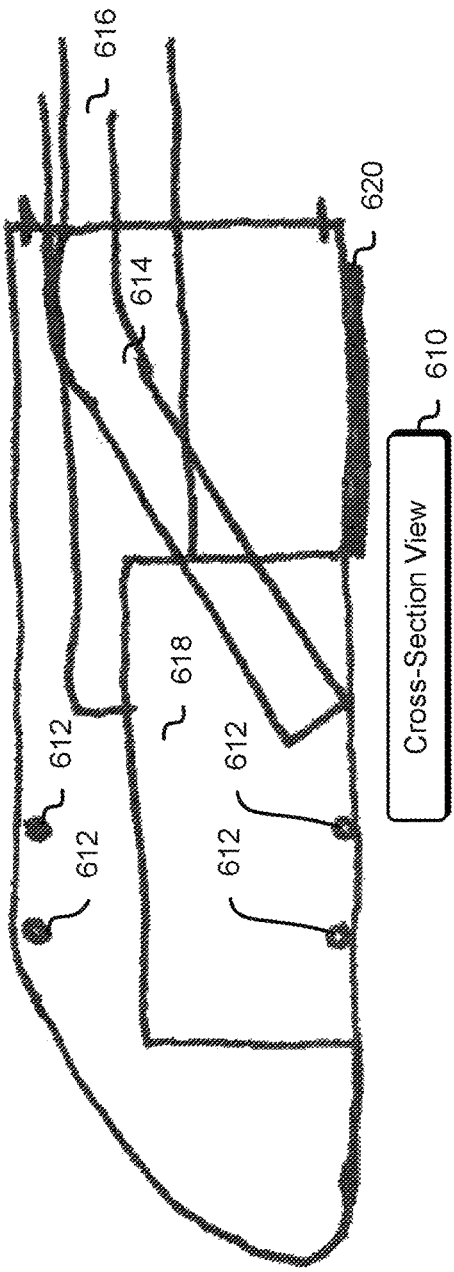
FIG. 6A Side View
FIG. 6B Cross-Section View

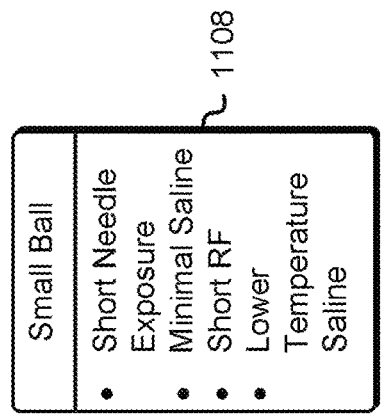
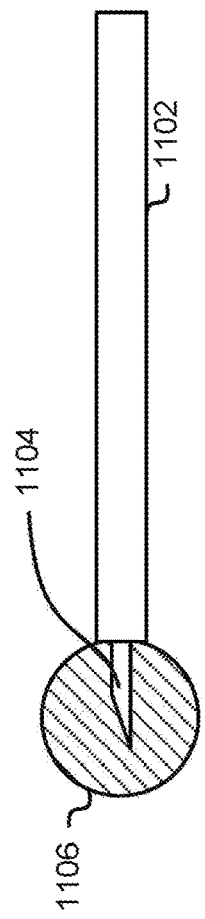
FIG. 11A
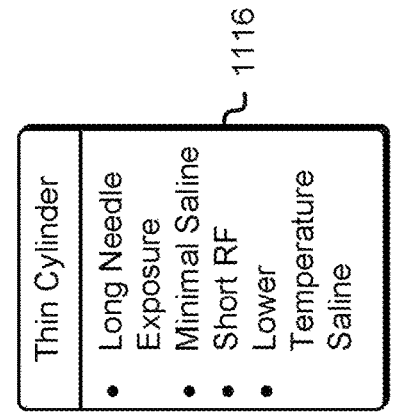
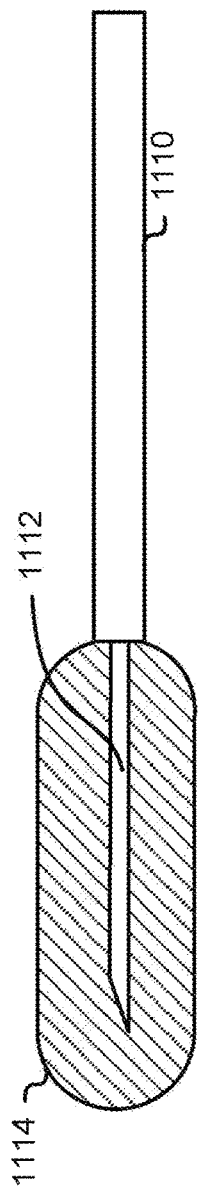
FIG. 11B

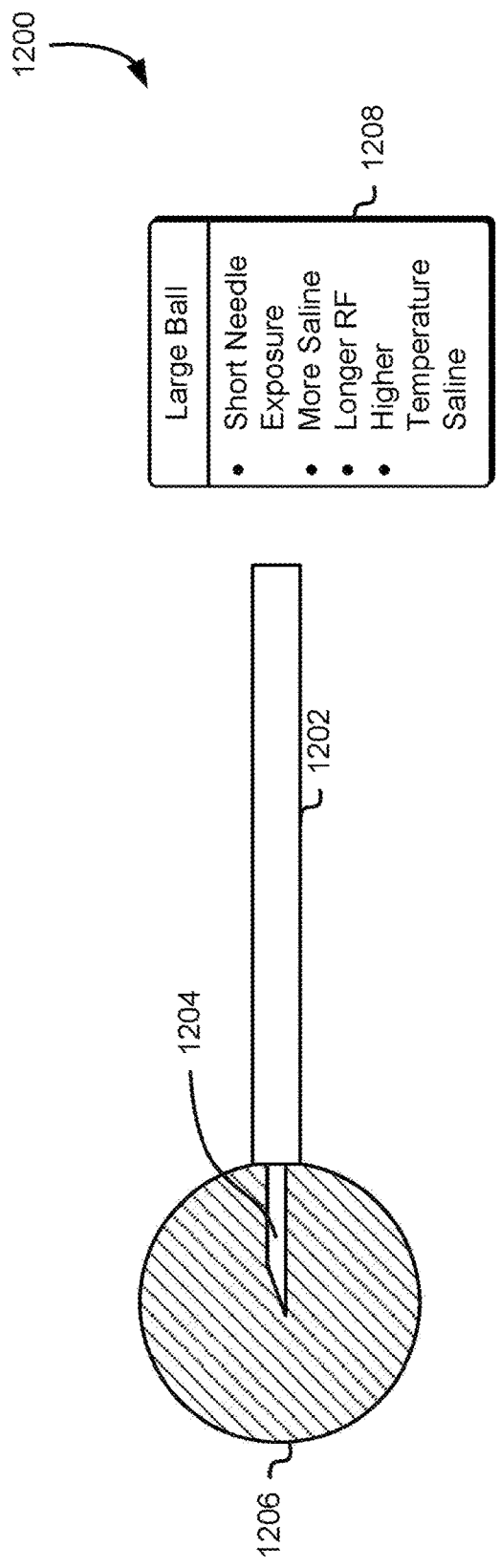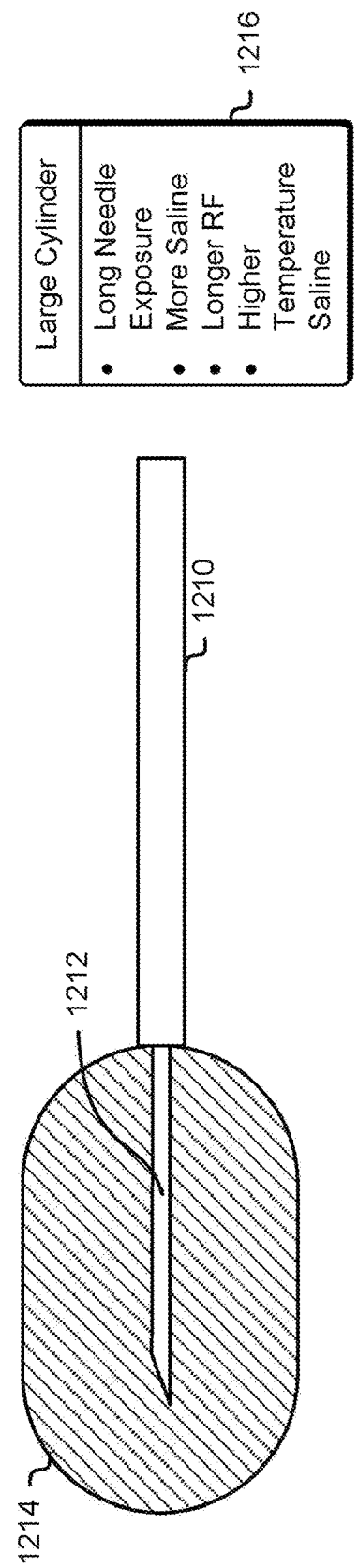
FIG. 12A
FIG. 12B

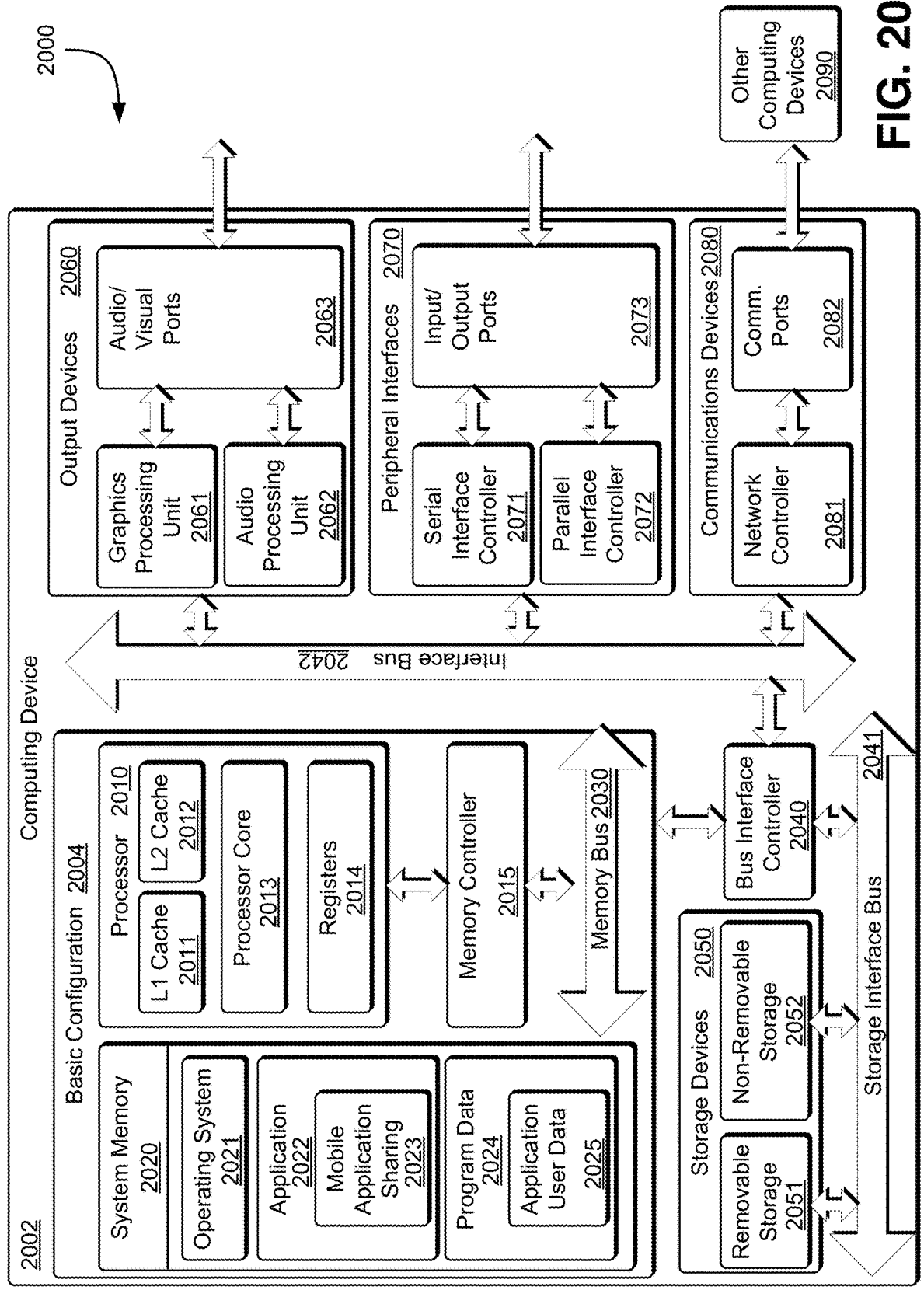

THERAPY DELIVERY SYSTEM THAT OPERATES ON THE SURFACE OF AN ANATOMICAL ENTITY

RELATED APPLICATIONS

This application is related to U.S. Provisional Application No. 62/170,097, filed on Jun. 2, 2015, entitled "THERAPY DELIVERY SYSTEM THAT OPERATES ON THE SURFACE OF AN ANATOMICAL ENTITY," the content of which is incorporated by reference herein in its entirety for all purposes.

BACKGROUND

An easier to use, less expensive, safer, more effective, and more widely applicable radiofrequency ablation ("RFA") treatment for ventricular tachycardia ("VT") is needed.

VT and related Ventricular Fibrillation ("VF") are associated with increased morbidity and mortality and account for an estimated 63% of the 180 k-450 k annual cases of sudden cardiac death in the US. Antiarrhythmic drugs, the first line treatment, do not eliminate VT, can worsen symptoms, can be harmful to other organs, and are expensive for both patient and insurer. So, patients with life-threatening VT are frequently treated with an implantable cardioverter-defibrillator ("ICD") that terminates but does not prevent VT. ICDs are expensive ($30,000 plus implantation cost), last at most 5-7 years, and provide limited overall mortality reduction of 1-3%. The possibly frequent shocks are painful, and associated with anxiety and depression. Reducing ICD shock frequency is a major objective of ablation therapy.

RFA can eliminate the triggers and substrate for VT and reduce/prevent consequent ICD shocks in patients at high risk of sudden cardiac death. However, current RFA procedures are lengthy and require great technical skill, and so are only performed at select specialized centers. Precise ablation of the VT circuit typically requires activation, pace, or entrainment mapping that, in turn, typically requires prolonged maintenance of VT for the needed measurements. Since this is rarely possible in patients with hemodynamically untolerated VTs, precise RFA techniques are unsuitable for the 70-80% of VTs that are fast and/or hemodynamically unstable. Assist devices to enable these patients to receive RFA (e.g., Tandem Heart® or Impella®) are impractically expensive (about $20K) and may increase thrombus risk. The final alternative is for patients to undergo substrate mapping which typically requires a time consuming procedure done by highly specialized electrophysiologists ("EP") needing to use rather large ablations to ensure success. Clearly, the majority of VT patients cannot benefit from the demonstrated quality of life improvements from RFA using current RFA techniques.

A typical RFA VT procedure costs around $15K in 2000 (~$20K today); >55% of which is the cost of developing the electrophysiological map. Because high skill is required to manipulate an endocardial ablation catheter precisely, emboli and complication rates have been estimated to be 6-8%. More precise ablations may reduce the risk of subsequently developing new reentrant circuits via remodeling. Revision is required in 12-20% of cases within two years. So even in the hands of the most skilled, experienced EP, the current procedures' success is less than it could be.

Thus, the combination of limitations in the currently addressable patient population and the difficulty in carrying out the procedure need to be transcended to bring RFA to the wider VT patient population.

BRIEF DESCRIPTION OF THE DRAWINGS

Various embodiments in accordance with the present disclosure will be described with reference to the drawings, in which:

FIGS. 4A-4C illustrate views of an example internal anatomy therapy delivery device;

FIGS. 5A-5C illustrate views of an example internal anatomy therapy delivery device;

FIGS. 6A and 6B illustrate views of an example internal anatomy therapy delivery device;

FIGS. 11A and 11B illustrate an example environment where an internal anatomy therapy delivery device delivers therapy in accordance with an embodiment;

FIGS. 12A and 12B illustrate an example environment where an internal anatomy therapy delivery device delivers therapy in accordance with an embodiment;

FIG. 20 illustrates an environment in which various embodiments can be implemented.

DETAILED DESCRIPTION

Figure 1:
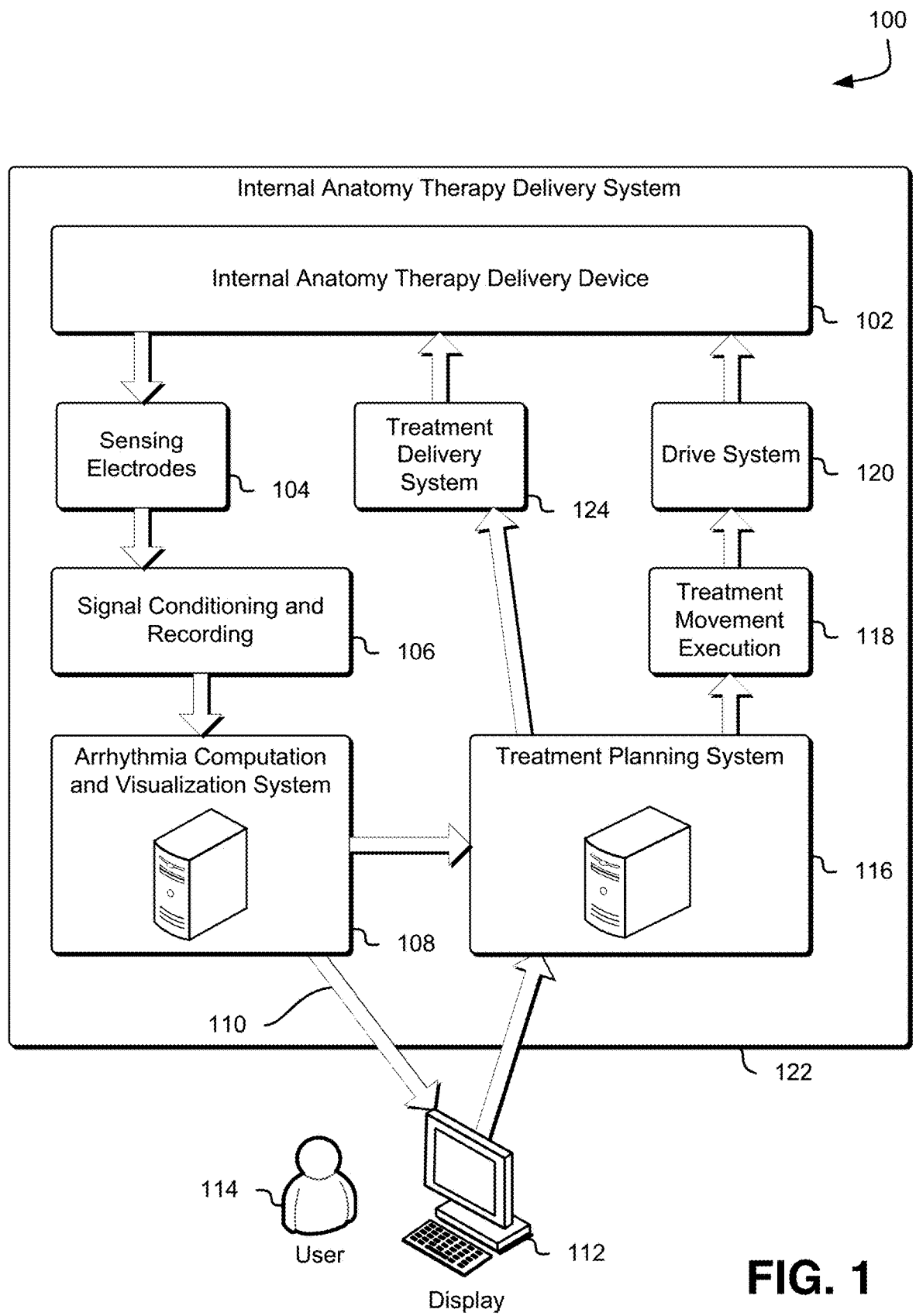
FIG. 1 illustrates an example environment where an internal anatomy therapy delivery system delivers therapeutic procedures in accordance with an embodiment.

Current RFA approaches to stopping VT from occurring typically involve some form of manual, by-hand mapping of the electrophysiological behavior of the heart during VT, the EP determining a treatment planning based on her interpretation of the information, and then her manually navigating a endocardial catheter to carry out the ablation of specific tissue sites believed to be the cause of the observed behaviors. This process is typically iterative with multiple re-executions of the same steps to affirm and refine the prior treatments in a session.

The solution described here takes a different approach. Firstly, it works from the epicardial surface rather than the endocardial chamber, with the myocardium providing a stable platform upon which to navigate about the heart surface. Second, it uses a walker that stably, reproducibly moves across that myocardial surface starting with a minimally invasive subxyphoid approach to place the walker through the pericardium and upon the myocardial surface. Third, it uses a unique signal processing approach that identifies arrhythmia sources directly. Fourth, it uses the same signal system used for the arrhythmia location to localize and guide the walker to that location. Fifth, it uses a needle-based RFA technique that is augmented with heated saline to allow a varying sizes and geometries of lesions to be created at varying depths within the myocardium. Sixth, it uses a Doppler ultrasound system to ensure that the needle does not pass close to a coronary vessel. Seventh, the needle placement is computed based on the arrhythmia location and nearby vessels to allow the walker to be automatically placed in the location that allows safe, accurate insertion of the needle to deliver the desired RFA.

This collection of capabilities system is the result of a combination of four technologies that enables this new approach to treating VT. First is the adaptation of the robotic HeartLander™ ("HL") epicardial walker for this application. Second is the use of the Single Equivalent Moving Dipole Mapping ("SEMDM") to track the HL walker's orientation and location in the same "sensor space" as the arrhythmia site so the walker can easily (optionally autonomously) be navigated to above the exact ablation site (SEMDM works in 3D so depth of the lesion target is known). Third the HL walker can insert a needle to a controlled depth into the myocardium and create a well conscribed lesion using saline-enhanced radiofrequency ablation ("SERF"). Fourth the system uses a Doppler flow ultrasound sensor ("DUS") embedded in the walker to detect and avoid coronary vessels.

The disposable HL walker serves as the primary therapy mapping and delivery device with sensors and delivery devices on board the walker to support the mission of using RFA to stop the occurrence of VT. The walker is supported by a reusable support system to which it is attached that provides locomotion, measurement of location, and delivery of RFA. The details of these components follow.

Figure 2:
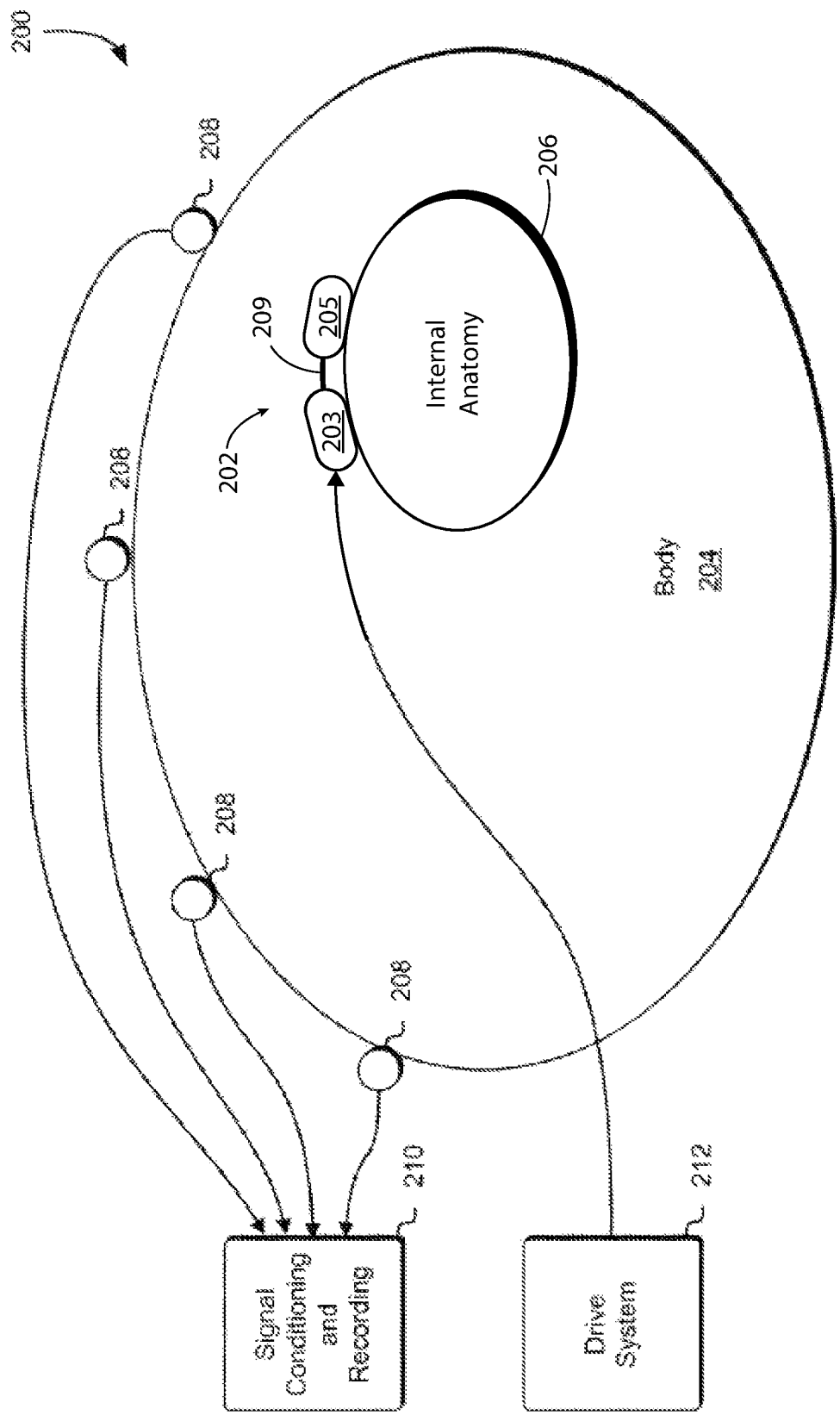
FIG. 2 illustrates an example environment where an internal anatomy therapy delivery device delivers therapeutic procedures in accordance with an embodiment.

Navigation. The HL consists of a miniature "walking" robot connected through a flexible tether to supporting instruments. This allows the therapeutic portion of the robot (the "walker") to be small, robust, and lightweight. As shown in FIG. 2, The walker consists of two tandem bodies 203, 205, the distance between which can be changed >2 cm by push-wires that run through the tether 209, connecting the front body to off-board actuation. Each body contains an independent suction chamber to create traction on the heart during locomotion or stable fixation. Vacuum, which can be safely applied to the epicardium, is supplied by lines through the tether. For example, as shown in FIG. 5, drive wires 508 and a suction line 504 extend through a tether 509. The locomotion of HL is a cyclic, inchworm-like process generated by alternating the direction of wire displacement between the two bodies 203, 205 and the vacuum in the two suction chambers.

Once placed on the apex of the heart via percutaneous, subxyphoid insertion through the pericardium using currently available placement devices, the system uses a set of movement rules to plan a series of steps to advance the walker toward a target or can be manually guided.

Mapping. SEMDM method can eliminate the need to develop a detailed EP map before an ablation procedure. It uses eight strips of electrodes with eight sensors on each that are placed approximately equally spaced around the chest to collect time-based ECG data to locate a concentrated charge front (e.g., reentrant circuit exit point or arrhythmogenic origin) in three dimensions relative to the sensor array in a what is called the sensor or image space using an Inverse Solution Guidance Algorithm based on a Single Equivalent Moving Dipole ("SEMD") model. Essentially, the algorithm finds a single dipole location and orientation that provides a statistical maximum in accounting for the signals observed by the sensors. This equivalent dipole is an effectively localizer of arrhythmias when they are distinct in the time sequence of depolarization wave front moving across the heart and when the arrhythmia itself is singularly unique.

In multiple academic studies, the SEMDM has been shown to identify dipole location, orientation, and depth within the myocardium. SEMDM requires data from only a few beats of VT to analyze dipole pose; HL-walker-based pacing can be used to initiate and terminate VT if needed. Position and orientation of the HL walker is determined in the same sensor space by using the electrodes embedded in the HL walker to stimulate the heart without initiating VT. The HL walker can then be guided to the arrhythmia origin dipole while the patient is in sinus rhythm. The SEMDM "sensor space" is distorted by factors such as variable chest anatomy, but the errors decline as the distance between walker and target decrease. To increase accuracy, the walker can pause and re-locate itself periodically relative to the target arrhythmia. Because the patient is in VT only for the initial localization of the arrhythmia dipole, a dramatically larger candidate pool of VT patients can be eligible for RFA.

Prior work with the HL walker as well as with endocardial catheters has shown SEMDM can be used to precisely navigate to a VT arrhythmogenic site. HL's on-board sensing combined with SEMD location information can also be used to generate multiple types of other widely used arrhythmia mapping techniques to augment the SEMDM arrhythmia targeting approach, e.g. voltage, LAVA (local abnormal ventricular activities), pace, activation, entrainment and other substrate techniques.

Ablation. Saline-enhanced radiofrequency ablation ("SERF") is known to create precise lesions with smooth edges and minimum collateral damage in cardiac tissue. The SERF approach used here has the ability to tightly control the volume of tissue ablated while also producing more uniform ablations. Injected, warmed saline allows the thermal energy from the RF to become more uniformly distributed, avoiding the overheating of tissues ("pops" and "char") near the needle that can happen with irrigated endocardial RF catheter systems. By adjusting needle depth, amount of the conductive portion of the needle exposed, saline flow and temperature, and RF characteristics, differing lesion geometries can be produced. This allows the HL's small needle to create precise, predictably sized, small, and large lesions. As part of the system, the impedance of the exposed needle tip is used to monitor the depth of the needle so that the placement of the lesion within the myocardial wall is controlled.

Vessel Avoidance. Endocardial ablation catheters are typically blind to vascular anatomy and risk damaging important veins and arteries when large transmural lesions need to be created. The HL-based walker system detects and avoids major coronary arteries and veins, even sub-surface ones, by using a thin film Doppler flow ultrasound sensor ("DUS") attached to the walker body and held in contact with the myocardial surface. The walker is programmed to scan the surface of the myocardium, collecting Doppler blood flow and SEMDM data to build a map of vessels in the vicinity of the ablation target and then use the map to plan needle-insertion tracks that avoid this vasculature.

In the preceding and following description, various techniques are described. For purposes of explanation, specific configurations and details are set forth in order to provide a thorough understanding of possible ways of implementing the techniques. However, it will also be apparent that the techniques described below may be practiced in different configurations without the specific details. Furthermore, well-known features may be omitted or simplified to avoid obscuring the techniques being described.

FIG. 1 illustrates an example environment 100 where an internal anatomy therapy delivery system 122 delivers therapeutic procedures in accordance with an embodiment. In the example illustrated in FIG. 1, an internal anatomy therapy delivery device 102 of the internal anatomy delivery system collects information via the sensing electrodes 104 and passes the data to the signal conditioning recording subsystem 106 where it is made ready for use in the arrhythmia computation and visualization system 108. For the specific embodiment described here, the voltage magnitudes of the electrical signals over time at the surface of the patient's chest are used by the arrhythmia computation and visualization system 108. In this specific embodiment, these signals are passed through an inverse computation to determine the single equivalent moving dipole for the signals. The user 114 observes the output of the computations from 108 via display 112 and interacts with the treatment planning system 116 to come up with a plan to be followed by the internal anatomy therapy delivery device 102. In the embodiment described here, this encompasses the output of the SEMD computation which yields a location where internal anatomy therapy delivery device 102 will want to move to deliver therapy. This movement is planned out by the treatment movement execution system 118 which in turn commands the drive system 120 on how to move the internal anatomy therapy delivery device 102. Once the internal anatomy therapy delivery device 102 reaches its goal location as defined by the treatment movement execution system 118, it will activate the treatment delivery system 124 to provide the requested therapy delivery at the requested location in a safe and effective manner.

FIG. 2 illustrates an example environment 200 where an internal anatomy therapy delivery device 202 delivers therapeutic procedures as described in connection with FIG. 1 and in accordance with an embodiment. In the example illustrated in FIG. 2, an internal anatomy therapy delivery device 202 delivers therapy to internal anatomy 206. This delivery is guided by information collected by sensors 208 which are distributed upon the body 204 within which the internal anatomy 206 is located. The signals sensed by sensors 208 are passed to the signal conditioning and recording system 210 where they can subsequently be used to plan the therapy delivery that will be carried out by the drive system 212. In one specific embodiment described here, the internal anatomy therapy delivery device 202 will be an epicardial walking device that is guided by electrical signals collected by the sensors 208 to provide direction for the drive system 212 which is causing the epicardial walking device to move across the surface of the heart.

Figure 3:
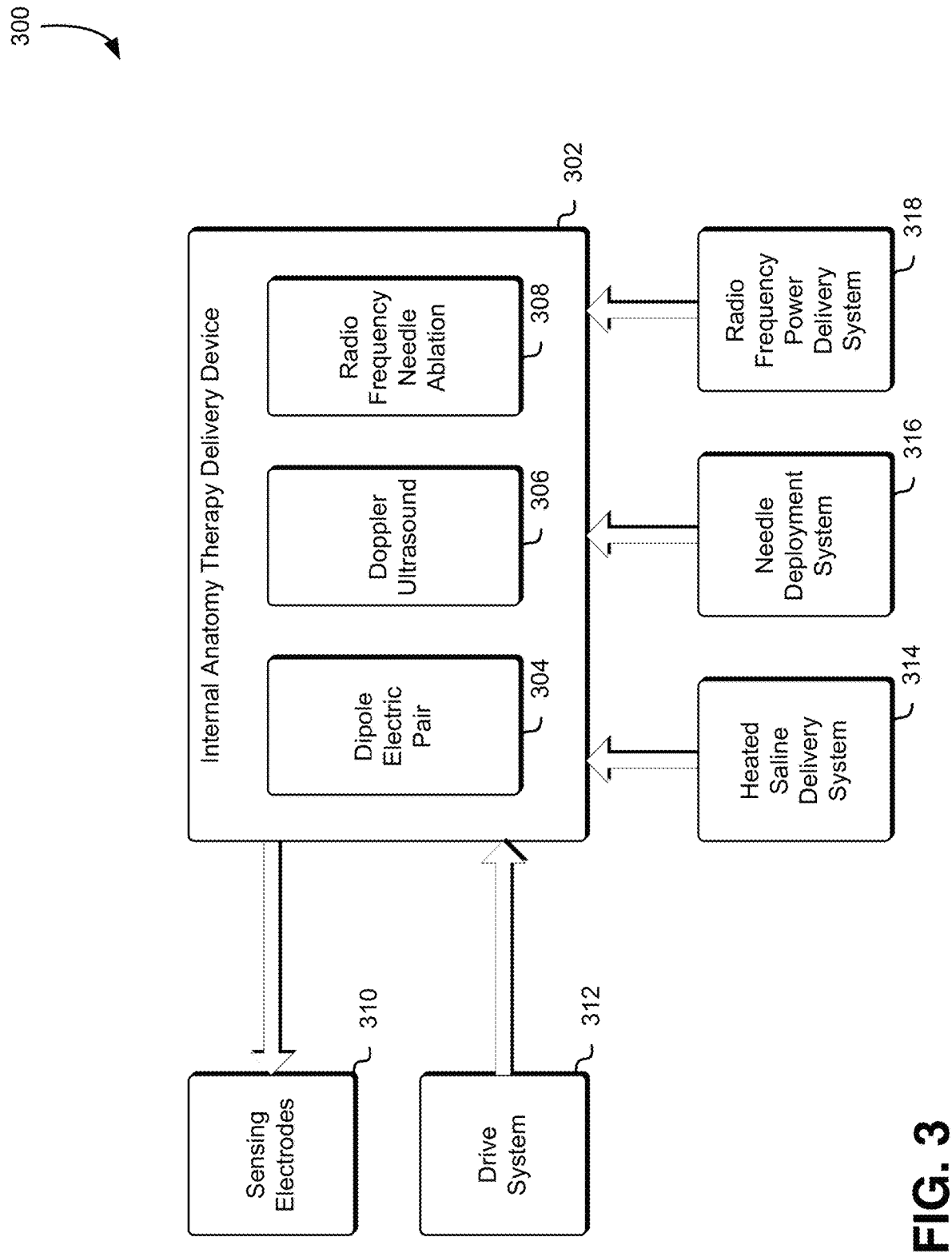
FIG. 3 illustrates an example environment where an internal anatomy therapy delivery device performs therapeutic procedures in accordance with an embodiment.

FIG. 3 illustrates an example environment 300 where an internal anatomy therapy delivery device 302 performs therapeutic procedures as described in connection with FIG. 1 and in accordance with an embodiment. In the example illustrated in FIG. 3, the internal anatomy therapy delivery device 302 consists of a number of systems. An internal anatomy therapy delivery device 302 delivers therapy based on sensor information provided by it via the sensing electrodes 310. This information includes the dipole electrode pair 304 and Doppler ultrasound 306 along with other information about the state of the environment surrounding the internal anatomy therapy delivery device 302 which is then combined and processed by a treatment plan to decide upon what is to be executed. In this specific embodiment, the systems that carry out the treatment plan include the drive system 312, the heated saline delivery system 314, the needle deployment system 316, and the radio frequency power delivery system 318. These systems enable the internal anatomy therapy delivery device 302 in this embodiment provide radio frequency ablation for treating ventricular tachycardia.

In FIGS. 4, 5, and 6, details of an example an internal anatomy therapy delivery device 102 are explained through several views and cross sections within those views.

FIGS. 4A-4C illustrate example views 400 of an internal anatomy therapy delivery device as described in connection with FIG. 1 and in accordance with an embodiment. In the example illustrated in FIGS. 4A-4C, multiple views are shown of the internal anatomy therapy delivery device 102 to explain its details. In the back view 402, the rear of the internal anatomy therapy delivery device 102 is shown. The main device body 426 consists of a material compatible with being in contact with the myocardium upon which it will walk. The internal anatomy therapy delivery device is moved by three drive wires attach to it at the back 408. It is selectively held to the myocardium by suction applied to it through the suction line connected to its back 404. Therapy is delivered by a needle-based delivery system, described in FIG. 7, which is fed into and whose deployment is controlled by the guide tube connected to the back of the internal anatomy therapy delivery device 406. Finally, the internal anatomy therapy delivery device has the ability to observe the myocardium beneath it to look for the presence of coronary vessels using the embedded Doppler ultrasound transducer 410.

FIGS. 5A-5C illustrate example views 500 of an internal anatomy therapy delivery device as described in connection with FIG. 1 and in accordance with an embodiment. In the example illustrated in FIGS. 5A-5C, multiple views are shown of the internal anatomy therapy delivery device to explain its details. In the top view 502, the internal anatomy therapy delivery device body 532 of the internal anatomy therapy delivery device is made of a material compatible with being in contact with the myocardium upon which it will walk. Within the internal anatomy therapy delivery device is a suction chamber that selectively keeps it in contact with the myocardium and is controlled by the suction line 504 that enters the rear of the internal anatomy therapy delivery device. A therapy delivery needle assembly enters the internal anatomy therapy delivery device body through a needle guide tube 506. This internal anatomy therapy delivery device is moved across the myocardium using three drive wires 508. A pair of conductive electrodes 510 and 512 is attached around the circumference of the rounded body of the internal anatomy therapy delivery device. These are used to form a bipolar signal pair to emit electrical waveforms as part of the navigation sensing system. The outer two wires entering the internal anatomy therapy delivery device body 532 pass through it and are connected together to form a continuous wire loop 514. This allows the two ends of the wire emerging from the internal anatomy therapy delivery device body 532 to be firmly attached to it. The final middle wire is independently glued and optionally mechanically connected to the internal anatomy therapy delivery device body 532.

The bottom view 516 of the internal anatomy therapy delivery device shows the suction chamber 520 to which the suction line 504 is connected. The needle guide path inside the internal anatomy therapy delivery device body 534 passes into the suction chamber 520 to enable the needle assembly that is brought into it by the needle guide tube 506 to pass through it on its way to entering the myocardium. A pair of electrodes passes around the internal anatomy therapy delivery device body 534 circumference, ending at the edges of the suction chamber 520 such that their ends 522 are seen from the bottom view. A Doppler ultrasound transducer 540 is attached to the bottom to enable observation of the presence of blood vessels beneath the internal anatomy therapy delivery device body 534.

The cross section view 524 of the internal anatomy therapy delivery device body 536 shows the suction chamber 538 as well as the suction supply path 526 that enables it to selectively attach to the myocardial surface. It also shows the needle assembly guide path that passes through the internal anatomy therapy delivery device body 536 and enables the needle assembly to be inserted into the myocardium through the suction chamber 538.

FIGS. 6A and 6B illustrate example views 600 of an internal anatomy therapy delivery device as described in connection with FIG. 1 and in accordance with an embodiment. In the example illustrated in FIGS. 6A and 6B, multiple views are shown of the internal anatomy therapy delivery device to explain its details. The side view 602 shows the internal anatomy therapy delivery device body 622 with pair of electrodes 604 and 606 going around its circumference. The Doppler ultrasound sensor 608 enables the internal anatomy therapy delivery device to detect coronary vessels beneath it. The cross section view 610 shows a cut away section down the middle of the internal anatomy therapy delivery device body 624. The electrodes 612 are seen passing at the top and bottom of the internal anatomy therapy delivery device body 624. On the bottom they terminate at the edge of the suction chamber 618 that enables the internal anatomy therapy delivery device to maintain firm contact with the myocardial surface. The chamber is supplied with its suction by 616 which allow it to selectively stay firm connected to the myocardium. The needle assembly guide path 614 allows the needle assembly to pass through the internal anatomy therapy delivery device body 624 into the suction chamber 618 so that the needle assembly can be pushed into the myocardium. Finally, the Doppler ultrasound transducer 620 allows the internal anatomy therapy delivery device to detect the presence of coronary vessels beneath it.

Figure 7:
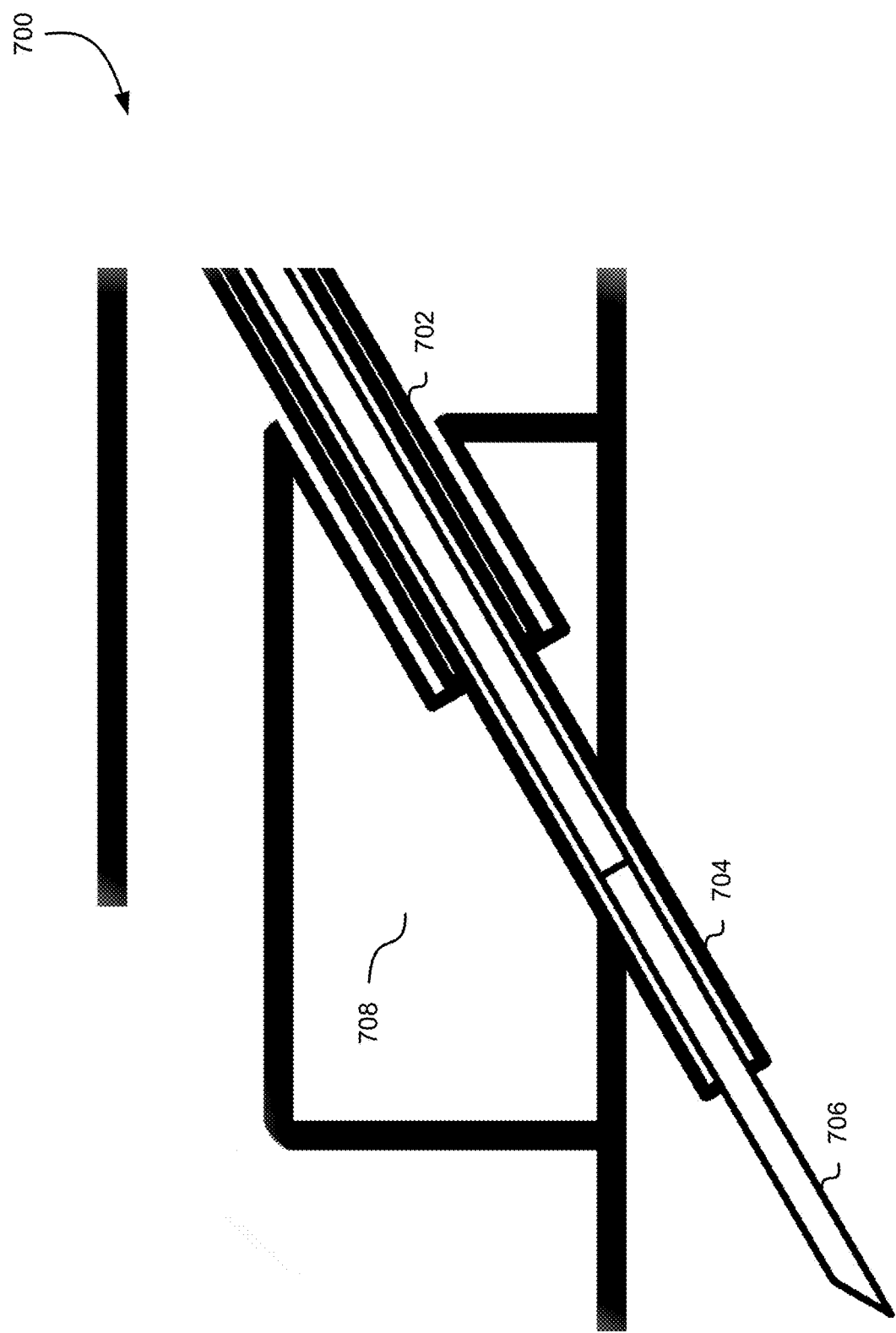
FIG. 7 illustrates an example environment where an internal anatomy therapy delivery device delivers therapy in accordance with an embodiment.

FIG. 7 illustrates an example environment 700 where an internal anatomy therapy delivery device delivers therapy in accordance with an embodiment. In the example illustrated in FIG.7, a needle assembly guide 702 that is part of the body of the anatomy therapy delivery device 710 has passing through a needle assembly consisting of a needle tip 706 and an insulator sheath 704. The needle assembly guide is within the suction chamber 708 so that the needle assembly can pass into the myocardium to which the suction chamber is attached. FIG. 7 is missing.

Figure 8:
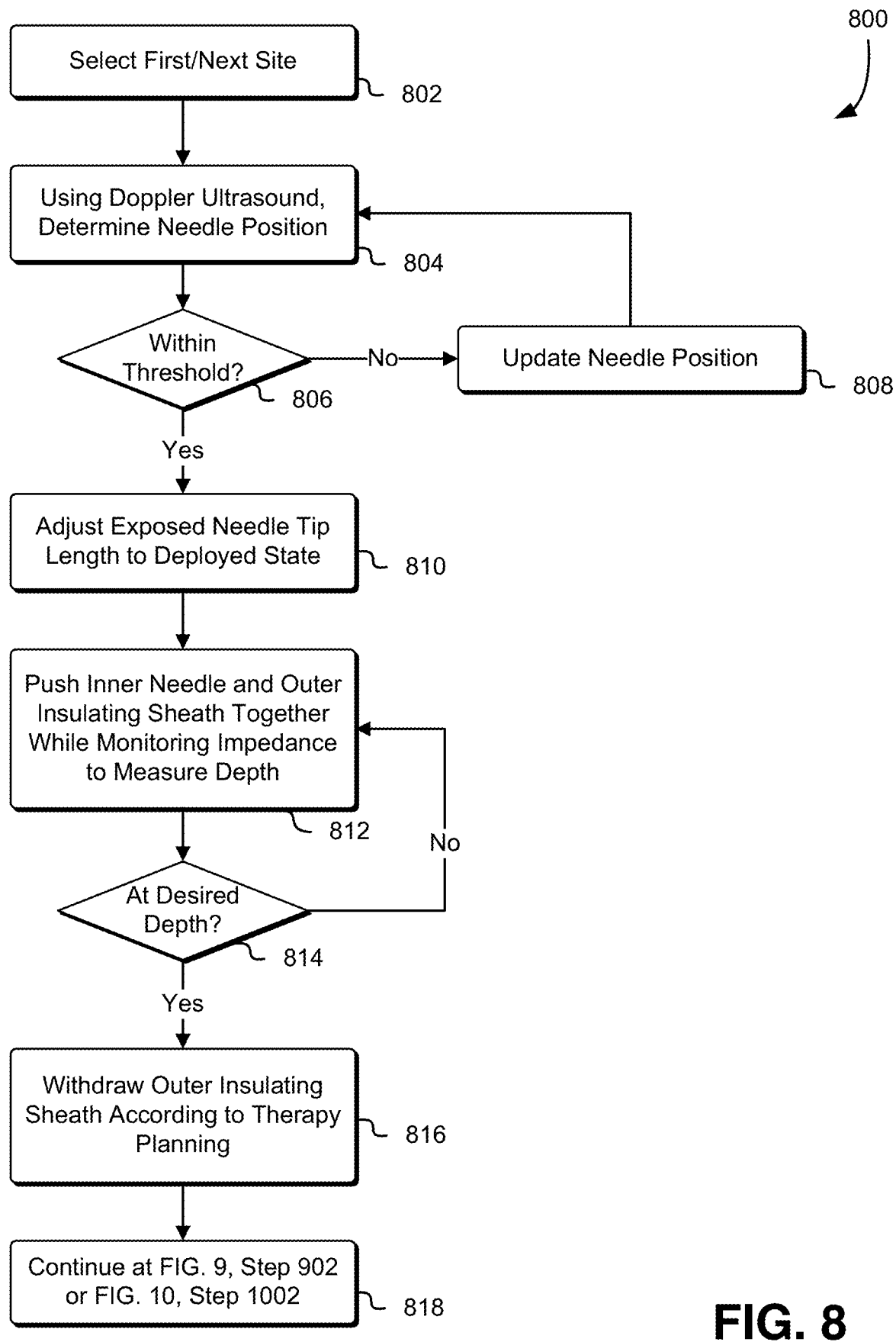
FIG. 8 illustrates a first portion of an example process for creating a lesion at a specific location with a specific geometry using an internal anatomy therapy delivery device in accordance with an embodiment.

FIG. 8 illustrates a first portion 800 of an example process for creating a lesion at a specific location with a specific geometry using an internal anatomy therapy delivery device as described in connection with FIG. 1 and in accordance with an embodiment. In the example illustrated in FIG. 8, the internal anatomy therapy delivery system 122 may first select 802 the first site for therapy delivery. At this first site, the Doppler ultrasound sensor embedded upon the internal anatomy therapy delivery device 102 will be used in combination with the software in 122 to plan out a needle path 804 to follow for deployment where a lesion will be created. Should this needle path pass within a threshold distance of a blood vessel 806 then updated needle path will be planned 808 and the process of determining if a path satisfying the threshold distance may be repeated. This sequence of events will be repeated until a path is found.

With the path determined, the metal needle tip and its outer insulator sheath will be deployed such that a specified length of the needle tip is exposed beyond the sheath 812. This exposed tip along with the sheath will then be simultaneously deployed such that a constant length of the needle tip is exposed beyond the insulator sheath while monitoring the impedance of the tissue at the needle tip until an impedance is measured that corresponds to the desired deployment depth. Upon reaching that depth 814, the exposed portion of the needle will be adjusted to provide the desired conductive length to produce the desire lesion geometry 816. Once this is done, the process continues in FIG. 9 or in FIG. 10.

Figure 9:
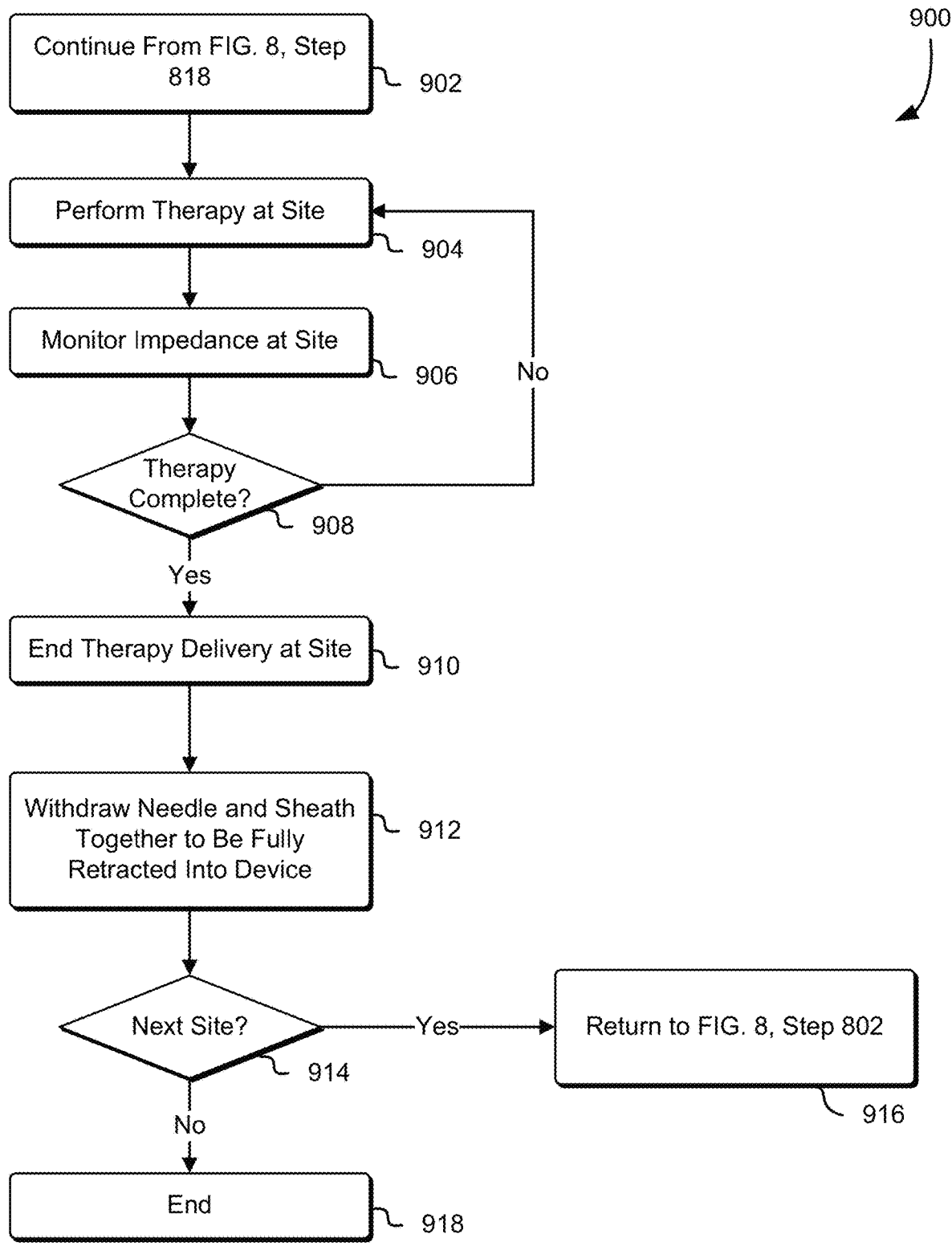
FIG. 9 illustrates a second portion of an example process for creating a lesion at a specific location with a specific geometry using an internal anatomy therapy delivery device in accordance with an embodiment.

FIG. 9 illustrates a second portion 900 of an example process for creating a lesion at a specific location with a specific geometry using an internal anatomy therapy delivery device as described in connection with FIG. 1 and in accordance with an embodiment. The second portion 900 of the example process is a continuation of the first portion 800 of the example process illustrated in FIG. 8. Continuing 902 from step 818 of FIG. 8, the internal anatomy therapy delivery device will next perform therapy 904 at the site located in 806. In performing therapy some needle-based delivery of therapy is performed while monitoring the measured change in a physical quantity 906 until the value of that quantity is such that therapy delivery is complete 908. With the end of therapy 910, the needle and sheath are withdrawn together 912 such that they are fully retracted into the passageway in the walker body so that the needle is no longer in contact with the myocardial tissue. Should there be another therapy delivery site identified 914, then the walker will move to that location and begin 916 the process illustrated in FIG. 8 again. Should there not be another therapy delivery site identified 914, the process will end 918.

Figure 10:
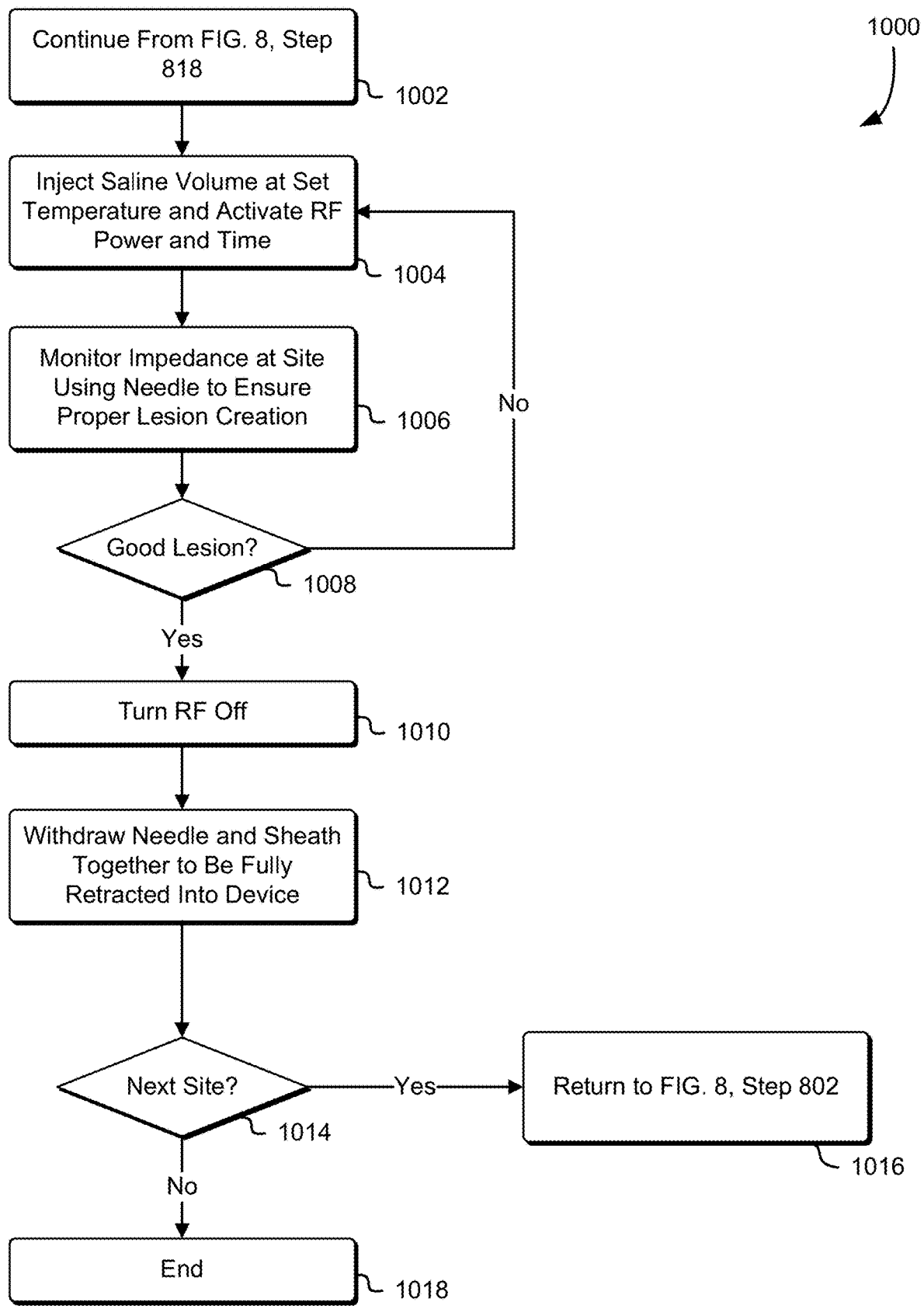
FIG. 10 illustrates a third portion of an example process for creating a lesion at a specific location with a specific geometry using an internal anatomy therapy delivery device in accordance with an embodiment.

FIG. 10 illustrates a third portion 1000 of an example process for creating a lesion at a specific location with a specific geometry using an internal anatomy therapy delivery device as described in connection with FIG. 1 and in accordance with an embodiment. The third portion 1000 of the example process is a continuation of the first portion 800 of the example process illustrated in FIG. 8. Continuing from step 818, the internal anatomy therapy delivery device 102 will next perform therapy 1004 at the site located in 806. An embodiment of performing therapy is to inject a desired volume of saline heated to a desired temperature and apply radio frequency ablation energy of a desired power for a desired time to denature myocardial tissue such that it can no longer conduct charge nor initiate an electrical wave front propagation. The means by which confirmation of this denaturing of the tissue is confirmed is by the change in impedance monitored 1006 such that when it reached a desired value the therapy delivery is complete 1008. With the end of therapy the RF energy is turned off 1010 and the needle and sheath are withdrawn together 1012 such that they are fully retracted into the passageway in the walker body so that the needle is no longer in contact with the myocardial tissue. Should there be another therapy delivery site identified 1014, and then the walker will move to that location and begin 1016 the process illustrated in FIG. 8 again. Should there not be another delivery site identified 1014, the process will end 1018.

FIGS. 11A and 11B illustrate an example environment 1100 where an internal anatomy therapy delivery device delivers therapy as described in connection with FIG. 1 and in accordance with an embodiment. The needle sheath assembly that is a part of the internal anatomy therapy delivery device is inserted into the myocardial tissue. In the case of the small ball lesion by adjusting relative position of the insulator sheath 1102 to the conductive metal needle tip 1104. By combining 1108 this short needle exposure with minimal heated saline injection, lower power RF ablation application, and lower saline temperature, a small ball shaped region 1106 of the lesion can be produced. In a similar approach, by having the conductive needle tip 1112 extend a longer distance beyond the insulator, while maintaining a similar injection volume at the needle tip will yield long, thin, cylindrical lesion. By combining 1116 this long needle exposure with minimal heated saline injection, lower power RF ablation application, and lower saline temperature, a long, thin cylindrically shaped region of the lesion can be produced.

FIGS. 12A and 12B illustrates an example environment 1200 where an internal anatomy therapy delivery device delivers therapy as described in connection with FIG. 1 and in accordance with an embodiment. In the example environment 1200 illustrated in FIGS. 12A and 12B, the needle sheath assembly that is a part of the internal anatomy therapy delivery device is inserted into the myocardial tissue. In the case of the larger ball lesion 1206, by adjusting relative position of the insulator sheath 1202 to the conductive metal needle tip 1204 and combining 1208 this with a substantial heated saline injection and higher power RF ablation application, a large ball shaped region of the lesion can be produced. In a similar approach, by having the conductive needle tip 1212 extend a longer distance beyond the insulator, while 1214 maintaining a similar injection volume at the needle tip will yield long, thin, cylindrical lesion. By combining 1216 this long needle exposure with minimal heated saline injection, lower power RF ablation application, and lower saline temperature, a long, thick cylindrically shaped region 1214 of the lesion can be produced.

Figure 13:
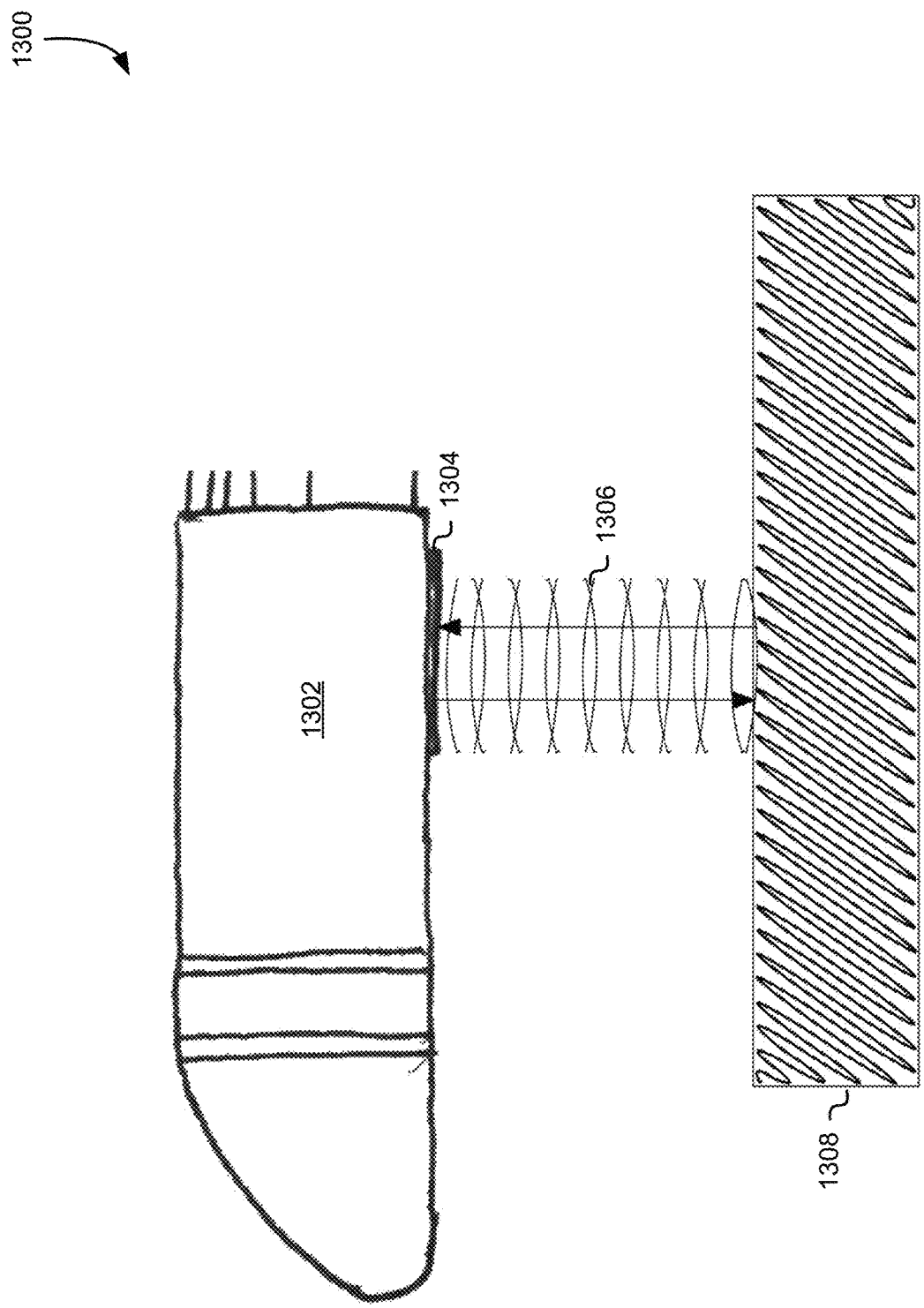
FIG. 13 illustrates an example environment where an internal anatomy therapy delivery device uses an embedded Doppler ultrasound sensor in accordance with an embodiment.

FIG. 13 illustrates an example environment 1300 where an internal anatomy therapy delivery device uses an embedded Doppler ultrasound sensor as described in connection with FIG. 1 and in accordance with an embodiment. In the example illustrated in FIG. 13, a thin film Doppler ultrasound sensor 1304 is attached to the bottom of the internal anatomy therapy delivery device body 1302. The Doppler ultrasound sensor sends ultrasound signals 1306 to detect the presence or not of a coronary blood vessel 1308 underneath it. Based on the detected presence or not of moving fluids beneath it, the decision will be made as whether to insert a radio frequency ablation needle.

Figure 14:
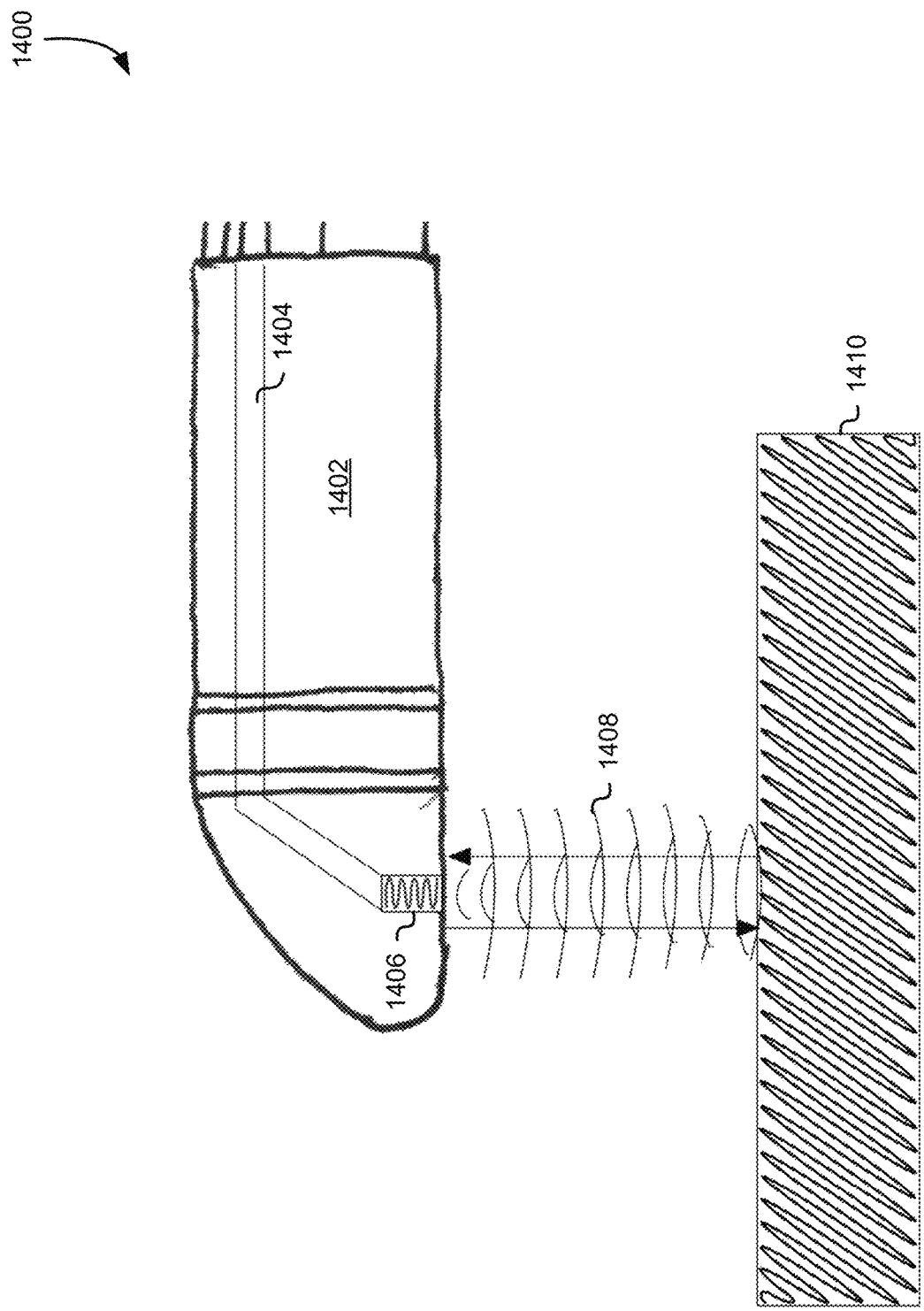
FIG. 14 illustrates an example environment where an internal anatomy therapy delivery device uses an embedded Doppler ultrasound sensor in accordance with an embodiment.

FIG. 14 illustrates an example environment 1400 where an internal anatomy therapy delivery device uses an embedded Doppler ultrasound sensor as described in connection with FIG. 1 and in accordance with an embodiment. In the example illustrated in FIG. 14, a crystalline Doppler ultrasound sensor 1406 is attached to the bottom of the internal anatomy therapy delivery device body 1402. This is an alternative sensor configuration compared to that in FIG. 13. The Doppler ultrasound sensor sends ultrasound signals 1408 to detect the presence or not of a coronary blood vessel 1410 underneath it. The signal is generated and its result returned via cable 1404. Based on the detected presence or not of moving fluids beneath it, the decision will be made as whether to insert a radio frequency ablation needle.

Figure 15:
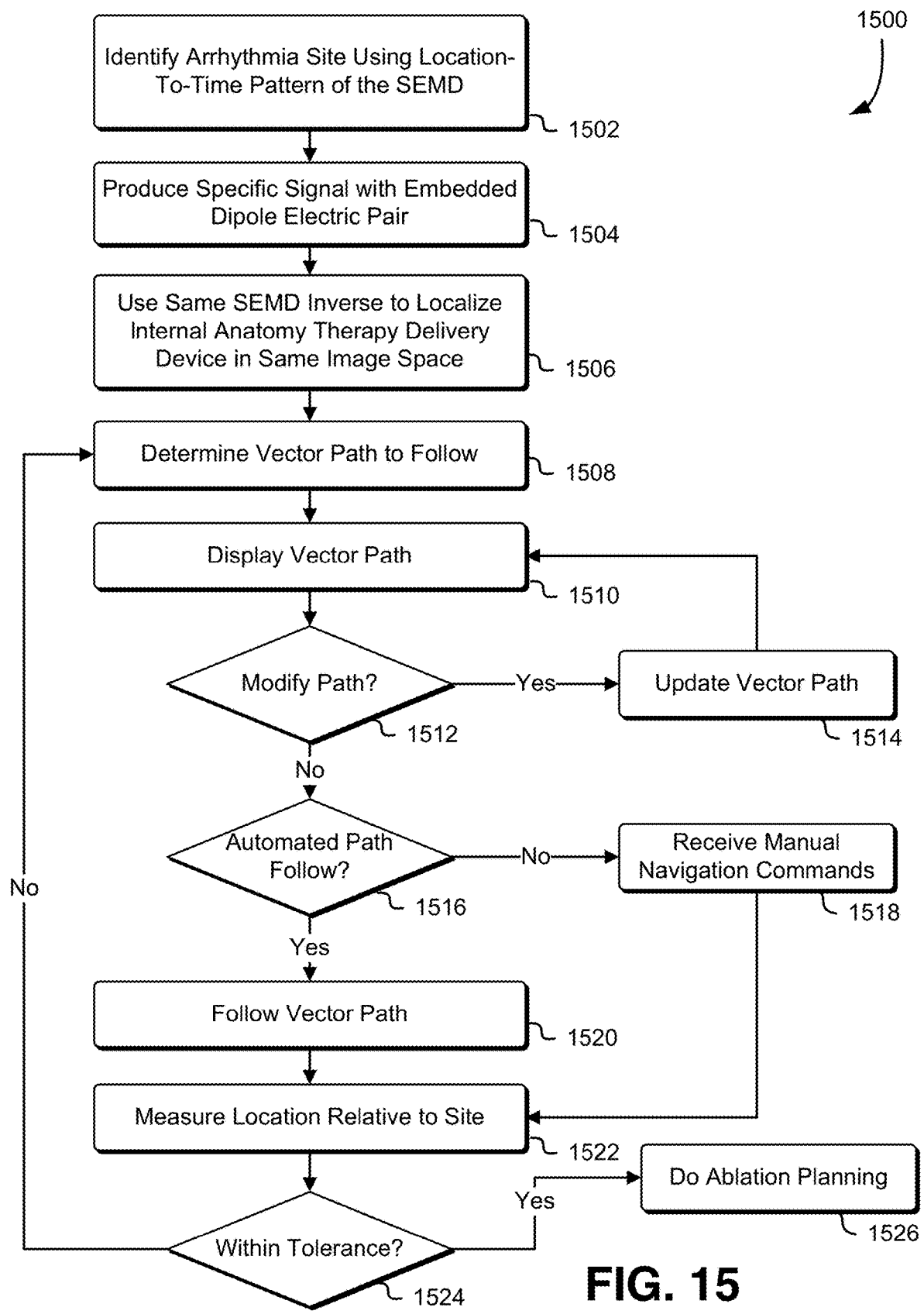
FIG. 15 illustrates an example process for navigating to the location of a site where arrhythmias are originating with an internal anatomy therapy delivery device in accordance with an embodiment.

FIG. 15 illustrates an example process 1500 for navigating to the location of a site where arrhythmias are originating with an internal anatomy therapy delivery device as described in connection with FIG. 1 and in accordance with an embodiment. The example illustrated in FIG. 15, begins with the location of the arrhythmia site being identified by the SEMD localization technique 1502. With that target location found, the internal anatomy therapy delivery device 102 uses its embedded dipole electrodes to send out a unique signal 1504 that can allow the same SEMD technique to localize it in the same image space in which the arrhythmia site is known 1506. Next the relative vector path leading from the present location of the internal anatomy therapy delivery device 102 to the location of the arrhythmia site is computed 1508 and this path is displayed to the user 1510 for potential modification 1512 and should the user decide to change the path 1514, they are presented with this new path and the process repeated until the user is satisfied. Once the user is satisfied, the internal anatomy therapy delivery device 102 may move toward the arrhythmia site under either automated or manual control of the user 1516. Should the user choose to manually control the internal anatomy therapy delivery device 102, they will use a provided user interface means to direct the movement 1518. Should the internal anatomy therapy delivery device 102 be set to follow an automated path, then it will commence its movement 1520. In both movement cases, periodic updates of the internal anatomy therapy delivery device's location are performed 1522 with the SEMD technique embodied in 1504 & 1506. With this updated location known, the relative position of the internal anatomy therapy delivery device 102 compared to the arrhythmia site and if it is within a desired tolerance of this distance 1524, then the movement is complete. Otherwise, the entire vector path following approach may be repeated. When the location of the internal anatomy therapy delivery device 102 is within the tolerance distance, then ablation planning can commence 1526 as described in FIG. 16.

Figure 16:
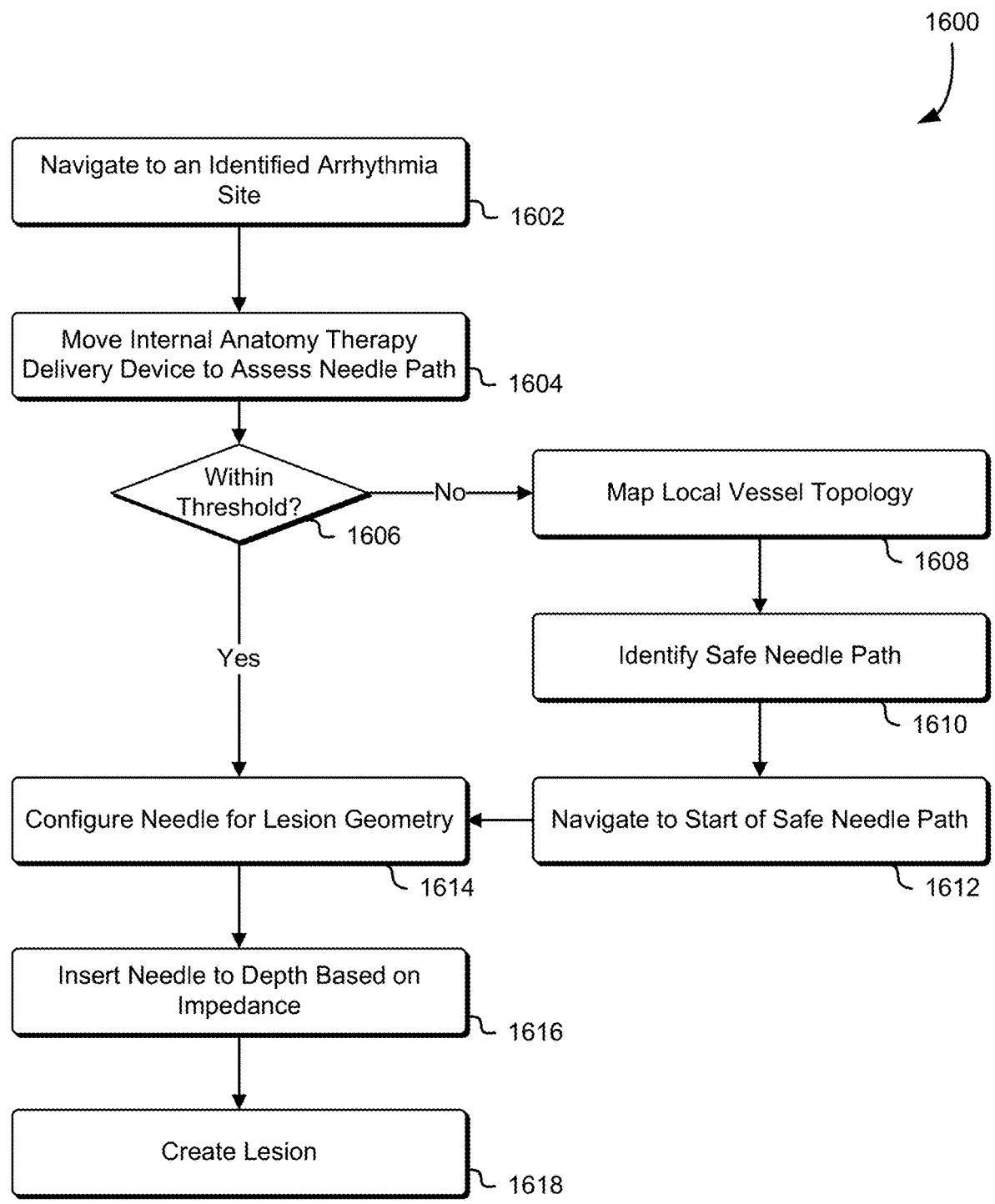
FIG. 16 illustrates an example process for planning out and creating a lesion at an arrhythmia site using an internal anatomy therapy delivery device in accordance with an embodiment.

FIG. 16 illustrates an example process 1600 for planning out and creating a lesion at an arrhythmia site navigated to by the processes described in FIG. 15 with an internal anatomy therapy delivery device as described in connection with FIG. 1 and in accordance with an embodiment. The example illustrated in FIG. 16, begins with the internal anatomy therapy delivery device 102 having navigated to the desired arrhythmia site to be treated 1602. Once there, the internal anatomy therapy delivery device 102 moves to compensate for the angle of the needle path that will be created relative to the bottom of its walker body such that the Doppler ultrasound sensor can observe the path to be followed by the needle 1604. Should no vessel be detected within a tolerance distance of the needle path 1606, then the lesion forming process may continue 1614. Should a vessel be detected, then the internal anatomy therapy delivery device 102 will perform a mapping of the area around the desired arrhythmia site to generate topological map of the vessels nearby 1608. Based upon this, a new needle path that keeps the needle at least the tolerance distance away from a vessel will be computed 1610 and then the internal anatomy therapy delivery device 102 moved to that safe location 1612 where the lesion forming process may continue 1614. The lesion forming process continues by configuring the exposure of the metal needle tip beyond the insulator sheath as detailed further in FIG. 8. The needle is then inserted to the desired depth into the myocardium using the change in tissue impedance to confirm the depth 1616. Once at that depth, the desired lesion geometry as described in FIGS. 11 and 12 can be created 1618.

Figure 17:
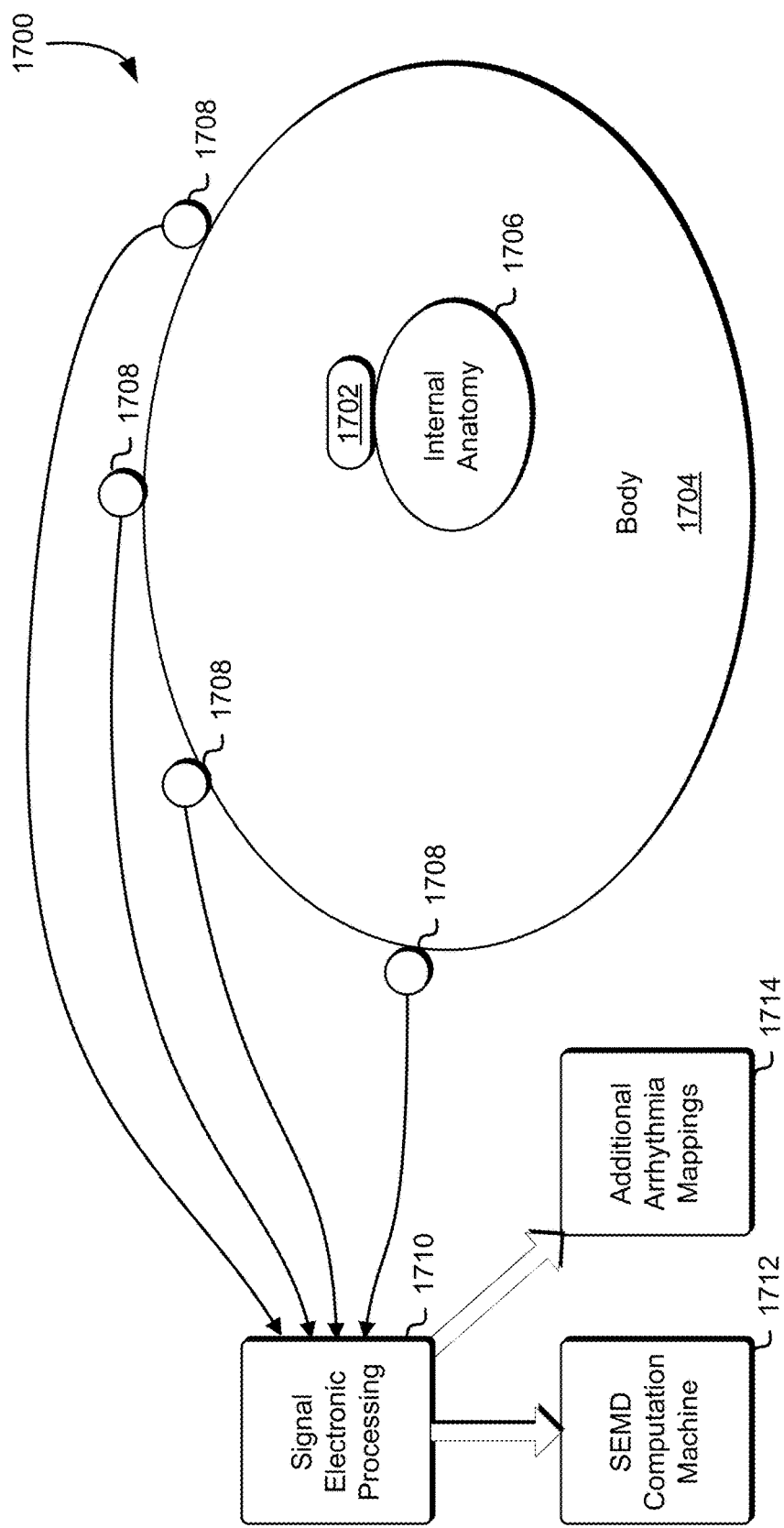
FIG. 17 illustrates an example environment where an internal anatomy therapy delivery system delivers therapeutic procedures in accordance with an embodiment.

FIG. 17 illustrates an example environment 1700 where an internal anatomy therapy delivery system delivers therapeutic procedures as described in connection with FIG. 1 and in accordance with an embodiment. In the example illustrated in FIG. 17, an internal anatomy therapy delivery device 1702 of the internal anatomy delivery system is moving to a therapy delivery location of interest on the internal anatomy 1706 which is located inside the body 1704. This delivery location is determined by a signal analysis method, either SEMD 1712 or one of a number of additional arrhythmia mappings 1714. The data used by these signal analysis approaches originates from electrodes which are placed on the outside of the body and record some signal reflective of a time varying state of a physical quantity within the body. One embodiment of this uses electrical signal electrodes 1708 to record the electrical potential on the body surface over time relative to a common ground. This signal is reflective of the propagation of charge across the heart and can be used as the input for the SEMD algorithm. These electrodes can be disposable and have either local amplification to minimize noise relative to the small magnitude of these signals or the signals can be converted into digital representations to be streamed via serial connection to electronic signal processing 1710.

Figure 18:
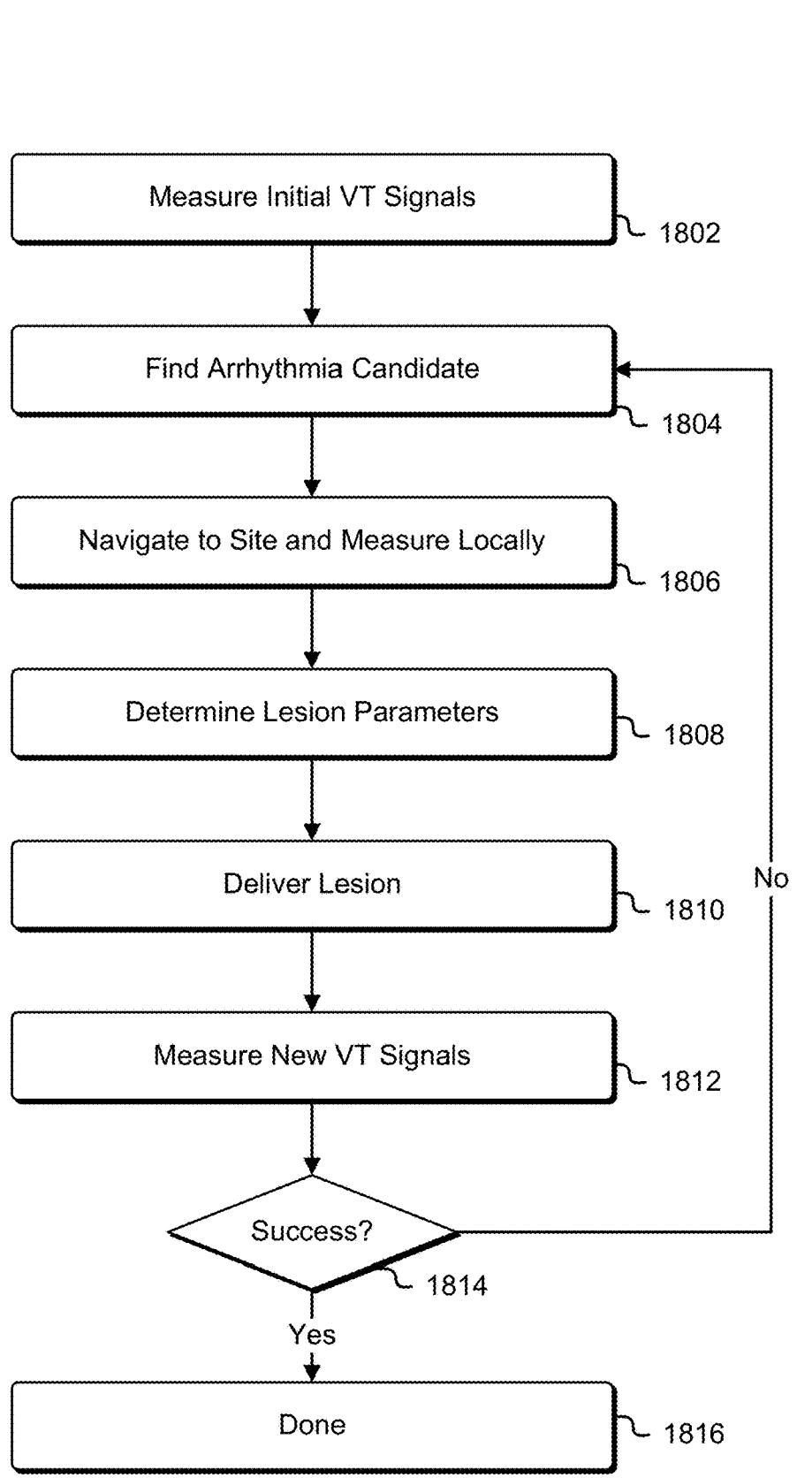
FIG. 18 illustrates an example process 1800 for eliminating ventricular tachycardia through the application of ablation to anatomic locations that are the source of the VT arrhythmias using an internal anatomy therapy delivery device in accordance with an embodiment.

FIG. 18 illustrates an example process 1800 for eliminating ventricular tachycardia through the application of ablation to anatomic locations that are the source of the VT arrhythmias using an internal anatomy therapy delivery device as described in connection with FIG. 1 and in accordance with an embodiment. The example begins with measuring the electrical signals at the surface of the patient's torso that are indicative of the behavior of the VT behavior 1802. The SEMD analysis approach or one of several other approaches is used to compute and identify a site where arrhythmia may be originating 1804. The internal anatomy therapy delivery device 102 then moves to the candidate site and it takes measurements at that location 1806 which are then used to decide upon the exact geometry of the lesion that will be created at the site 1808. The internal anatomy therapy delivery device 102 then delivers the combination of radio frequency energy and heated saline required to produce the desired lesion geometry 1810. Once this is complete, the electrical signals are measured again to see if VT is still present 1812. If it is, then the process of computing a candidate arrhythmia site and its treatment by ablation begins anew 1814. If there is no VT present, then the VT is considered to have been eliminated.

Figure 19:
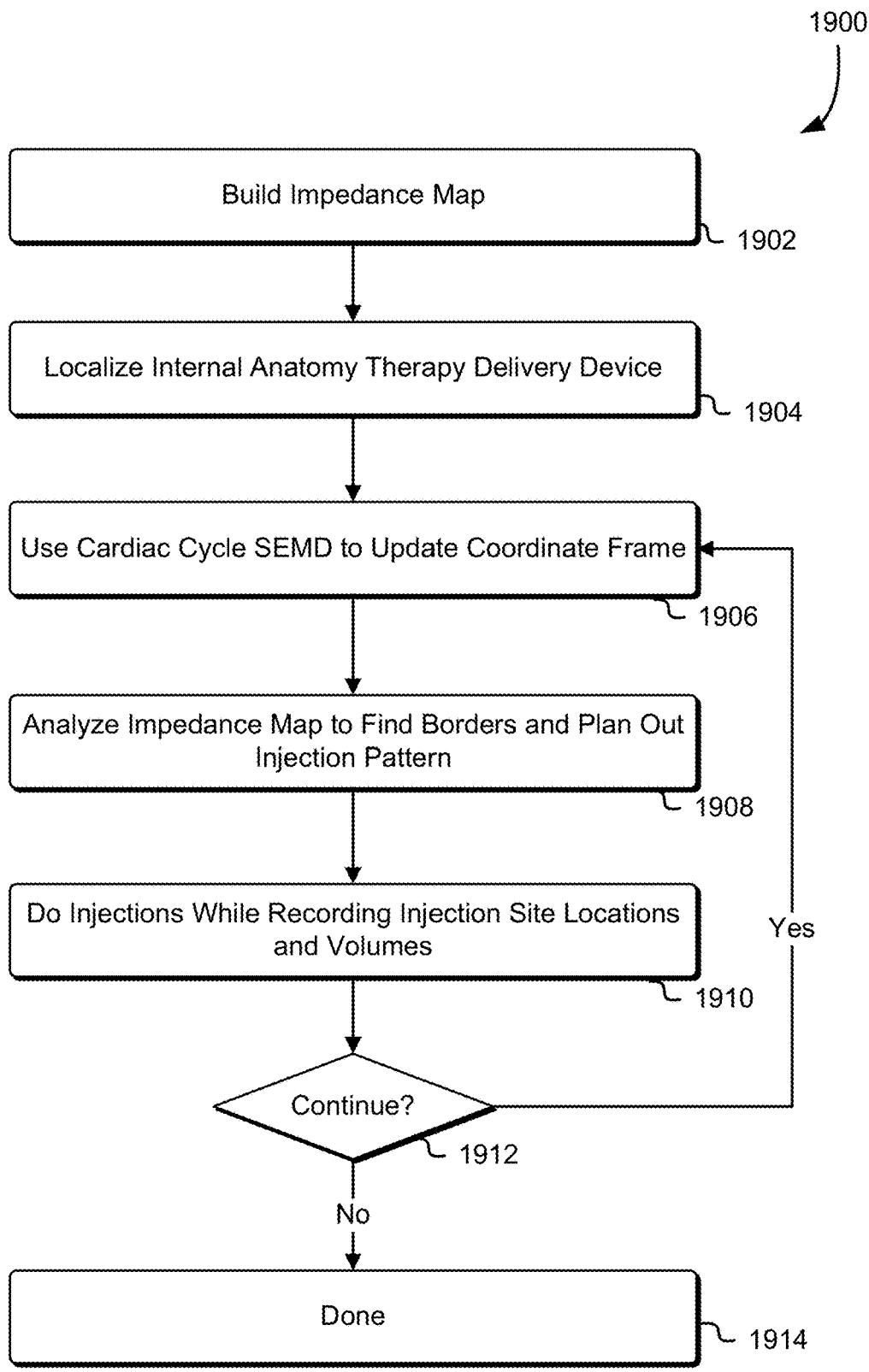
FIG. 19 illustrates an example process for delivering substances that can enable to a heart damaged from a myocardial infarction to regenerate its damaged tissue and hence return to function using an internal anatomy therapy delivery device in accordance with an embodiment.

FIG. 19 illustrates an example process 1900 for delivering substances that can enable to a heart damaged from a myocardial infarction to regenerate its damaged tissue and hence return to function using an internal anatomy therapy delivery device as described in connection with FIG. 1 and in accordance with an embodiment. The therapy is performed by the internal anatomy therapy delivery device 102 as described in FIG. 1. The device moves about upon the myocardial surface measuring the tissue impedance while simultaneously measuring its spatial location using the electrical signal electrodes 1708 (also referred to herein as "surface electrodes" or "electrodes on the anatomical surface") along with its associated signal conditioning and processing described in FIG. 17. The result is an impedance map 1902 that shows where infarcted tissue and normal tissue are located since the impedance of infarcted tissue is distinct from impedance of normal tissue. Unique relative to the measurement technique described in FIG. 15, the SEMD localization method is used to identify the location and orientation of the dipole that represents the start of the heart beat at the SA node 1906. This location is consistent from beat to beat as well as over long periods of time. Thus, this location can be used as a common reference frame between multiple therapy sessions over time. Taking the impedance map, the edges of the infarcted region can be identified 1908. With these edges known, locations distributed along this border can be identified and the internal anatomy therapy delivery device 102 can be navigated to each of these locations. At each location, it will use its ability to make safe injections to inject regeneration promoting substances, such as stem cells, into the myocardium while recording its location as it does the injection 1910. This provides a map of injection history if/when future regeneration injections are performed. This sequence of injections distributed over the myocardial surface continues 1912 until all desired sites have had regenerative substances applied to them 1914.

FIG. 20 illustrates an example environment 2000 with an example computing device 2002 that may be used to implement one or more embodiments, in accordance with the present disclosure. In a basic configuration 2004, an example computing device 2002 may include one or more processors 2010 and may include memory such as system memory 2020. A memory bus 2030 may be used for communicating between a processor 2010 of the computing device 2002 and the system memory 2020. The computing device 2002 may include any appropriate device operable to send and/or receive requests, messages, or information over an appropriate network and may, in some embodiments, convey information back to a user of the computing device in response to such requests. Examples of such computing devices include personal computers, cell phones, handheld messaging devices, laptop computers, tablet computers, set-top boxes, personal data assistants, mobile devices, wearable devices, embedded computer systems, electronic book readers, application specific client devices and the like. The network may include any appropriate network, including an intranet, the Internet, a cellular network, a local area network, a satellite network or any other such network and/or combination thereof. Communication over the network can be enabled by wired or wireless connections and combinations thereof The information (also referred to herein as "content") conveyed back to the user of the computing device 2002 may include, but may not be limited to, text, graphics, audio, video, and/or other content usable to be provided to the user. The information conveyed back to the user of the computing device may be conveyed in the form of HyperText Markup Language ("HTML"), Extensible Markup Language ("XML"), JavaScript, Cascading Style Sheets ("CSS"), or some other such client-side structured language. Content may be processed by the computing device 2002 to provide the content to the user of the computing device 2002 in one or more forms including, but not limited to, forms that are perceptible to the user audibly, visually and/or through other senses including touch, taste, and/or smell. Requests and responses sent over the network may be handled by a server using PHP: Hypertext Preprocessor ("PHP"), Python, Ruby, Perl, Java, HTML, XML, or another appropriate server-side structured language. It should be understood that operations described herein as being performed by a single device may, unless otherwise clear from context, be performed collectively by multiple devices.

In some embodiments, the processor 2010 may be of a type including but not limited to a microprocessor, a microcontroller, a digital signal processor (DSP), or any combination thereof. A processor 2010 may include one more levels of caching, such as a level one (L1) cache 2011 and a level two (L2) cache 2012. A processor may also include a processor core 2013, and registers 2014. The processor core 2013 may include, for example, an arithmetic logic unit (ALU), a floating point unit (FPU), a digital signal processing core (DSP Core), a graphics processing unit (GPU) or a combination of these and/or other such processing units. A memory controller 2015 may also be used with the processor 2010 to control the memory such as the system memory 2020. In some implementations the memory controller 2015 may be an internal part of the processor 2010.

In some embodiments, the system memory 2020 may be of any type including but not limited to volatile memory (such as RAM), non-volatile memory (such as ROM, flash memory, etc.) or any combination thereof. System memory 2020 may contain an operating system 2021, one or more applications 2022, and program data 2024 associated with such applications 2022. An application 2022 may include a component 2023 configured for sharing applications between mobile devices in a peer-to-peer environment, in accordance with the present disclosure. The program Data 2024 may include applicant or organizational data 2025 as described herein. In some embodiments, application 2022 can be arranged to operate with program data 2024 on an operating system 2021 such that operation of a system may be facilitated on general purpose computer systems.

A computing device 2002 can have additional features or functionality, and additional interfaces to facilitate communications between the basic configuration 2004 and any required devices and interfaces. For example, a bus/interface controller 2040 can be used to facilitate communications between the basic configuration 2004 and one or more data storage devices 2050 via a storage interface bus 2041. The data storage devices 2050 can be removable storage devices 2051, non-removable storage devices 2052, or a combination thereof. Examples of removable storage and non-removable storage devices include magnetic disk devices such as flexible disk drives and hard-disk drives (HOD), optical disk drives such as compact disk (CD) drives or digital versatile disk (DVD) drives, solid state drives (SSD), and tape drives and/or other such storage devices. Examples of computer storage media may include volatile and nonvolatile, removable and non-removable media implemented in any method or technology for storage of information, such as computer readable instructions, data structures, program modules, or other data.

System memory 2020, removable storage device 2051, and non-removable storage device 2052 are all examples of computer storage media. Computer storage media (or computer-readable medium) includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 2002. Any such computer storage media can be part of device 2002.

Computing device 2002 may also include an interface bus 2042 for facilitating communication from various interface devices (e.g., output interfaces, peripheral interfaces, and communication interfaces) to the basic configuration 2004 via the bus/interface controller 2040. Example output devices 2060 include a graphics processing unit 2061 and an audio processing unit 2062, which can be configured to communicate to various external devices such as a display or speakers via one or more audio/visual ports 2063. Example peripheral interfaces 2070 include a serial interface controller 2071 or a parallel interface controller 2072, which can be configured to communicate with external devices such as input devices (e.g., keyboard, mouse, pen, voice input device, touch input device, etc.) or other peripheral devices (e.g., printer, scanner, etc.) via one or more I/O ports 2073.

An example communication device 2080 may include a network controller 2081, which can be arranged to facilitate communications with one or more other computing devices 2090 over a network communication via one or more communication ports 2082. Communication ports 2082 may further include components configured to communicate over a near-area network. Examples of such communication ports 2082 may utilize at least one network for supporting communications using any of a variety of protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS") and Common Internet File System ("CIFS"). The network can be, for example, a local area network, a wide-area network, a virtual private network, the Internet, an intranet, an extranet, a public switched telephone network, an infrared network, a wireless network, a satellite network, and any combination thereof.

A computing device 2002 may be implemented as a computer such as a laptop computer, a personal computer, a workstation, a server or some other such computer device. A computing device 2002 may also be implemented as a portable (or mobile) computer such as a cell phone, a personal data assistant (PDA), a personal media player device, a wireless web-watch device, a personal headset device, an application specific device, or some other such device. A computing device may also be implemented as a combination of computer and/or portable devices including, but not limited to, the devices described herein. A computing device 2002 may include an operating system that may provide executable program instructions for the general administration and operation of that device and may include a computer-readable storage medium (e.g., a hard disk, random access memory, read only memory, etc.) storing instructions that, when executed by a processor of the device, allow the device to perform its intended functions.

The computing device 2002 illustrated in the example environment 2000 may be part of a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 20. Thus, the depiction of the system illustrated in FIG. 20 should be taken as being illustrative in nature and not limiting to the scope of the disclosure. The various embodiments may also be implemented in a wide variety of operating environments, which in some cases can include one or more computers and/or computing devices that may be used to operate any number of applications. Such devices may include any of a number of general purpose personal computers, such as desktop, laptop or tablet computers running a standard operating system, as well as cellular, wireless and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, application specific devices and other devices capable of communicating via a network. These devices also can include virtual devices such as virtual machines and other such virtual devices capable of communicating via a network.

Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings herein are to be regarded in an illustrative rather than a restrictive sense. It will, however, be evident that various modifications and changes may be made thereunto without departing from the broader spirit and scope of the invention as set forth in the claims.

Other variations are within the spirit, and therefore scope, of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Conjunctive language, such as phrases of the form "at least one of A, B, and C," or "at least one of A, B and C," unless specifically stated otherwise or otherwise clearly contradicted by context, is otherwise understood with the context as used in general to present that an item, term, etc., may be either A or B or C, or any nonempty subset of the set of A and B and C. For instance, in the illustrative example of a set having three members, the conjunctive phrases "at least one of A, B, and C" and "at least one of A, B and C" refer to any of the following sets: $\{A\}$, $\{B\}$, $\{C\}$, $\{A, B\}$, $\{A, C\}$, $\{B, C\}$, $\{A, B, C\}$. Thus, such conjunctive language is not generally intended to imply that certain embodiments require at least one of A, at least one of B and at least one of C each to be present.

The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Embodiments of this disclosure are described herein, including the best mode known to the inventors for carrying out the invention. Variations of those embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An internal anatomy therapy delivery system for performing radiofrequency ablation treatment for ventricular tachycardia, comprising:
an internal anatomy therapy delivery device comprising a proximal body flexibly connected to a distal body, wherein at least one body includes a Doppler ultrasound device configured to produce signals related to a presence of one or more coronary vessels and wherein the internal anatomy therapy delivery device is configured to generate a map of an area identifying a location of any of the one or more coronary vessels within the area based on the Doppler ultrasound signals;
an arrhythmia computation system comprising a first computing device configured to receive sensor data from the internal anatomy therapy delivery device, wherein the first computing device is further configured to calculate a location of an arrhythmia based on the sensor data;
a treatment planning system comprising a second computing device configured to:
provide treatment movement instructions to a drive system based on the location of the arrhythmia and the map, wherein the treatment movement instructions comprise a movement path for the internal anatomy therapy delivery device;
provide treatment delivery instructions to a treatment delivery system configured to deliver radiofrequency ablation treatments, wherein the treatment delivery instructions are based on the location of the arrhythmia and the map, wherein the treatment delivery instructions avoid delivery of the radiofrequency ablation treatments to the one or more coronary vessels based on the map, and wherein the treatment delivery system is attached to the internal anatomy therapy delivery device;
wherein the drive system comprises a third computing device configured to provide movement commands to the internal anatomy therapy delivery device, wherein the movement commands are based on the treatment movement instructions;
wherein the internal anatomy therapy delivery device is configured to walk on an epicardial surface;
wherein the internal anatomy therapy delivery device is further configured to perform the following actions:
move to the location of the arrhythmia based on the movement commands;
determine a set of lesion parameters based on one or more local measurements of the arrhythmia;
instruct the treatment delivery system to form a lesion using the radiofrequency ablation treatments, wherein the lesion is based on the set of lesion parameters; and
provide one or more new local measurements of the arrhythmia to the treatment planning system following a formation of the lesion; and
wherein the internal anatomy therapy delivery system is configured to plan out a needle path within the area for a needle of the internal anatomy therapy delivery device to follow for deployment from the internal anatomy therapy delivery device within the area to a location where the lesion will be created, and wherein the needle path satisfies a threshold distance from the any of the one or more coronary vessels within the area, the needle path being determined after the internal anatomy therapy delivery device moves to the location of the arrhythmia.

2. The system of claim 1, wherein the internal anatomy therapy delivery device further includes a dipole electric pair and a radio frequency needle ablation device, wherein the radio frequency needle ablation device comprises the needle.

3. The system of claim 2, wherein the dipole electric pair extends around a circumference of the internal anatomy therapy delivery device.

4. The system of claim 1, wherein the treatment delivery system comprises a heated saline delivery system, a needle deployment system, and a radio frequency power delivery system.

5. The system of claim 1, wherein the movement commands are calculated in a warp nonlinear image space.

6. The system of claim 1, wherein the sensor data is received from one or more sensor electrodes positioned proximate an external anatomy surface.

7. The system of claim 1, wherein the set of lesion parameters includes needle exposure.

8. The system of claim 1, wherein the system further comprises a tip of the needle and an insulator sheath, the tip of the needle and the insulator sheath being coupled to the internal anatomy therapy delivery device,
wherein the tip of the needle and the insulator sheath are simultaneously deployed such that a constant length of the tip of the needle is exposed beyond the insulator sheath while monitoring an impedance of a tissue at the tip of the needle until the impedance monitored corresponds to a desired deployment depth.

9. The system of claim 1, wherein the internal anatomy therapy delivery device further comprises a suction chamber and an insulator sheath, at least a portion of the needle being configured to pass through the insulator sheath, the needle and the insulator sheath being configured to pass through the suction chamber.

10. The system of claim 9, wherein the suction chamber is configured to couple the internal anatomy therapy delivery device to the epicardial surface while the internal anatomy therapy delivery device is moving.

11. The system of claim 1, wherein the proximal body is coupled to the distal body by a tether.

12. The system of claim 1, wherein the internal anatomy therapy delivery device is configured to move to compensate for an angle of the needle path that will be created relative to a bottom of the internal anatomy therapy delivery device such that the Doppler ultrasound device is configured to sense the needle path.

13. The system of claim 1, wherein the internal anatomy therapy delivery device is configured to walk on the epicardial surface by adhering the distal body to the epicardial surface while moving the proximal body then adhering the proximal body while moving the distal body.

14. The system of claim 1, wherein each of the proximal body and distal body comprises a suction chamber, and wherein the internal anatomy therapy delivery device is configured to walk on the epicardial surface by alternating vacuum between the suction chambers of the proximal and distal bodies and an alternating movement of the proximal and distal bodies.

15. The system of claim 1, wherein the internal anatomy therapy delivery device is elongated in a first direction, wherein the internal anatomy therapy delivery device is configured to walk on the epicardial surface such that the first direction is substantially parallel with the epicardial surface.

16. The system of claim 1, wherein the first computing device is further configured to receive the sensor data from sensors external to the internal anatomy therapy delivery device, wherein the first computing device is further configured to calculate the location of the arrhythmia and of the internal anatomy delivery device based on the sensor data.

17. The system of claim 1, wherein the Doppler ultrasound device is positioned on the proximal body and is configured to move relative to an ablation energy delivery surface.

18. The system of claim 1, wherein the map is configured to be created by fixing the proximal body to the epicardial surface and moving the distal body over the area to be mapped.

19. A system, comprising:
an internal anatomy therapy delivery device comprising a proximal body flexibly connected to a distal body, wherein at least one of the proximal body and the distal body includes a Doppler ultrasound device configured to produce signals related to a presence of one or more coronary vessels at a location and wherein the internal anatomy therapy delivery device is configured to generate a map of an area identifying the location of any of the one or more coronary vessels within the area based on the Doppler ultrasound device signals;
at least one computing device configured to implement one or more services, wherein the one or more services are configured to:
calculate a treatment location based on sensor data received from the internal anatomy therapy delivery device;
receive treatment delivery instructions based on a treatment, wherein the treatment corresponds to the treatment location, and wherein the treatment delivery instructions avoid a puncturing of and/or delivery of radiofrequency ablation to any of the one or more coronary vessels within the area covered by the map; and
provide movement commands based on treatment movement instructions, wherein the treatment movement instructions are based on the treatment location, and wherein the movement commands comprise a movement path for the internal anatomy therapy delivery device;
wherein the internal anatomy therapy delivery device is configured to walk on an anatomical surface, wherein the internal anatomy therapy delivery device is further configured to perform the following actions:
move to the treatment location based on the movement commands;
determine a set of treatment parameters based on a first set of local measurements of the anatomical surface;
instruct a treatment delivery system to deliver the treatment based on the set of treatment parameters; and
measure a second set of local measurements of the anatomical surface following delivery of the treatment; and
wherein the internal anatomy therapy delivery system further comprises a needle and is configured to plan out a needle path within the area for the needle to follow for deployment from the internal anatomy therapy delivery device within the area to the treatment location where the treatment will be delivered, and wherein the needle path satisfies a threshold distance from the any one of the one or more coronary vessels within the area,
the needle path being determined after the internal anatomy therapy delivery device moves to the treatment location.

20. The system of claim 19, wherein the one or more services are configured to calculate a location of an arrhythmia, and wherein the location of the arrhythmia comprises the treatment location.

21. The system of claim 19, wherein the system further comprises a treatment delivery system configured to receive the treatment delivery instructions.

22. The system of claim 19, wherein the movement path comprises a path operable on the anatomical surface.

23. The system of claim 22, wherein the anatomical surface comprises an epicardial surface.

24. The system of claim 23, wherein the map is configured to be created by fixing the proximal body to the anatomical surface and moving the distal body over the area to be mapped.

25. The system of claim 19, wherein the therapy delivery device is configured to determine the set of treatment parameters comprising a set of lesion parameters.

26. The system of claim 25, wherein the set of lesion parameters includes at least one of: a needle exposure; an amount of saline; a length of radiofrequency ablation; or a saline temperature.

27. The system of claim 19, wherein the treatment delivery system is configured to deliver the treatment which comprises a lesion.

28. The system of claim 19, wherein the internal anatomy therapy delivery device is further configured to perform the following action: determine the first set of local measurements of the anatomical surface that comprise local measurements of a ventricular tachycardia and measure the second set of local measurements of the anatomical surface that comprise local measurements of a ventricular tachycardia.

* * * * *